(12) United States Patent
Weingerten

(10) Patent No.: US 8,782,500 B2
(45) Date of Patent: Jul. 15, 2014

(54) SYSTEMS AND METHODS FOR ERROR CORRECTION AND DECODING ON MULTI-LEVEL PHYSICAL MEDIA

(71) Applicant: Densbits Technologies, Haifa (IL)

(72) Inventor: Hanan Weingerten, Herzelia (IL)

(73) Assignee: Densbits Technologies Ltd., Haifa (IL)

( * ) Notice: Subject to any disclaimer, the term of this patent is extended or adjusted under 35 U.S.C. 154(b) by 0 days.

(21) Appl. No.: 13/746,072

(22) Filed: Jan. 21, 2013

(65) Prior Publication Data
US 2013/0139037 A1    May 30, 2013

Related U.S. Application Data

(63) Continuation of application No. 12/667,043, filed as application No. PCT/IL2008/001229 on Sep. 17, 2008, now Pat. No. 8,359,516.

(60) Provisional application No. 61/071,487, filed on May 1, 2008, provisional application No. 61/071,468, filed on Apr. 30, 2008, provisional application No. 61/064,995, filed on Apr. 8, 2008, provisional application No. 61/006,385, filed on Jan. 10, 2008, provisional application No. 60/996,948, filed on Dec. 12, 2007.

(51) Int. Cl.
*H03M 13/00* (2006.01)
(52) U.S. Cl.
USPC ............................................. 714/785
(58) Field of Classification Search
CPC .. H04L 1/0057; H03M 13/116; H03M 13/19; G06F 11/1076
USPC .......................................... 714/752, 763, 777
See application file for complete search history.

(56) References Cited

U.S. PATENT DOCUMENTS

| | | |
|---|---|---|
| 4,430,701 A | 2/1984 | Christian et al. |
| 4,463,375 A | 7/1984 | Macovski |
| 4,584,686 A | 4/1986 | Fritze |
| 4,589,084 A | 5/1986 | Fling et al. |
| 4,777,589 A | 10/1988 | Boettner et al. |
| 4,866,716 A | 9/1989 | Weng |
| 5,003,597 A | 3/1991 | Merkle |
| 5,077,737 A | 12/1991 | Leger et al. |
| 5,297,153 A | 3/1994 | Baggen et al. |
| 5,305,276 A | 4/1994 | Uenoyama |
| 5,592,641 A | 1/1997 | Doyle et al. |
| 5,623,620 A | 4/1997 | Alexis et al. |
| 5,640,529 A | 6/1997 | Hasbun |
| 5,657,332 A | 8/1997 | Auclair et al. |
| 5,663,901 A | 9/1997 | Harari et al. |
| 5,724,538 A | 3/1998 | Morris et al. |

(Continued)

OTHER PUBLICATIONS

Search Report of PCT Patent Application WO 2009/118720 A3, Mar. 4, 2010.

(Continued)

*Primary Examiner* — Yolanda L Wilson
(74) *Attorney, Agent, or Firm* — Dentons US LLP

(57) ABSTRACT

Apparatus and methods for operating a flash device characterized by use of Lee distance based codes in a flash device so as to increase the number of errors that can be corrected for a given number of redundancy cells, compared with Hamming distance based codes.

23 Claims, 18 Drawing Sheets

(56) References Cited

U.S. PATENT DOCUMENTS

| | | |
|---|---|---|
| 5,729,490 A | 3/1998 | Calligaro et al. |
| 5,740,395 A | 4/1998 | Wells et al. |
| 5,745,418 A | 4/1998 | Hu et al. |
| 5,778,430 A | 7/1998 | Ish et al. |
| 5,793,774 A | 8/1998 | Usui et al. |
| 5,920,578 A | 7/1999 | Zook et al. |
| 5,926,409 A | 7/1999 | Engh et al. |
| 5,933,368 A | 8/1999 | Hu et al. |
| 5,956,268 A | 9/1999 | Lee |
| 5,956,473 A | 9/1999 | Hu et al. |
| 5,968,198 A | 10/1999 | Balachandran |
| 5,982,659 A | 11/1999 | Irrinki et al. |
| 6,011,741 A | 1/2000 | Harari et al. |
| 6,016,275 A | 1/2000 | Han |
| 6,038,634 A | 3/2000 | Ji et al. |
| 6,081,878 A | 6/2000 | Estakhri et al. |
| 6,094,465 A | 7/2000 | Stein et al. |
| 6,119,245 A | 9/2000 | Hiratsuka |
| 6,182,261 B1 | 1/2001 | Haller et al. |
| 6,192,497 B1 | 2/2001 | Yang et al. |
| 6,195,287 B1 | 2/2001 | Hirano |
| 6,199,188 B1 | 3/2001 | Shen et al. |
| 6,209,114 B1 | 3/2001 | Wolf et al. |
| 6,259,627 B1 | 7/2001 | Wong |
| 6,272,052 B1 | 8/2001 | Miyauchi |
| 6,278,633 B1 | 8/2001 | Wong et al. |
| 6,279,133 B1 | 8/2001 | Vafai et al. |
| 6,301,151 B1 | 10/2001 | Engh et al. |
| 6,370,061 B1 | 4/2002 | Yachareni et al. |
| 6,374,383 B1 | 4/2002 | Weng |
| 6,504,891 B1 | 1/2003 | Chevallier |
| 6,532,169 B1 | 3/2003 | Mann et al. |
| 6,532,556 B1 | 3/2003 | Wong et al. |
| 6,553,533 B2 | 4/2003 | Demura et al. |
| 6,560,747 B1 | 5/2003 | Weng |
| 6,637,002 B1 | 10/2003 | Weng et al. |
| 6,639,865 B2 | 10/2003 | Kwon |
| 6,674,665 B1 | 1/2004 | Mann et al. |
| 6,675,281 B1 | 1/2004 | Oh et al. |
| 6,704,902 B1 | 3/2004 | Shinbashi et al. |
| 6,751,766 B2 | 6/2004 | Guterman et al. |
| 6,772,274 B1 | 8/2004 | Estakhri |
| 6,781,910 B2 | 8/2004 | Smith |
| 6,792,569 B2 | 9/2004 | Cox et al. |
| 6,873,543 B2 | 3/2005 | Smith et al. |
| 6,891,768 B2 | 5/2005 | Smith et al. |
| 6,914,809 B2 | 7/2005 | Hilton et al. |
| 6,915,477 B2 | 7/2005 | Gollamudi et al. |
| 6,952,365 B2 | 10/2005 | Gonzalez et al. |
| 6,961,890 B2 | 11/2005 | Smith |
| 6,968,421 B2 | 11/2005 | Conley |
| 6,990,012 B2 | 1/2006 | Smith et al. |
| 6,996,004 B1 | 2/2006 | Fastow et al. |
| 6,999,854 B2 | 2/2006 | Roth |
| 7,010,739 B1 | 3/2006 | Feng et al. |
| 7,012,835 B2 | 3/2006 | Gonzalez et al. |
| 7,038,950 B1 | 5/2006 | Hamilton et al. |
| 7,068,539 B2 | 6/2006 | Guterman et al. |
| 7,079,436 B2 | 7/2006 | Perner et al. |
| 7,149,950 B2 | 12/2006 | Spencer et al. |
| 7,177,977 B2 | 2/2007 | Chen et al. |
| 7,188,228 B1 | 3/2007 | Chang et al. |
| 7,191,379 B2 | 3/2007 | Adelmann et al. |
| 7,196,946 B2 | 3/2007 | Chen et al. |
| 7,203,874 B2 | 4/2007 | Roohparvar |
| 7,212,426 B2 | 5/2007 | Park et al. |
| 7,290,203 B2 | 10/2007 | Emma et al. |
| 7,292,365 B2 | 11/2007 | Knox |
| 7,301,928 B2 | 11/2007 | Nakabayashi et al. |
| 7,315,916 B2 | 1/2008 | Bennett et al. |
| 7,388,781 B2 | 6/2008 | Litsyn et al. |
| 7,395,404 B2 | 7/2008 | Gorobets et al. |
| 7,441,067 B2 | 10/2008 | Gorobets et al. |
| 7,443,729 B2 | 10/2008 | Li et al. |
| 7,450,425 B2 | 11/2008 | Aritome |
| 7,454,670 B2 | 11/2008 | Kim et al. |
| 7,466,575 B2 | 12/2008 | Shalvi et al. |
| 7,533,328 B2 | 5/2009 | Alrod et al. |
| 7,558,109 B2 | 7/2009 | Brandman et al. |
| 7,593,263 B2 | 9/2009 | Sokolov et al. |
| 7,610,433 B2 | 10/2009 | Randell et al. |
| 7,613,043 B2 | 11/2009 | Cornwell et al. |
| 7,619,922 B2 | 11/2009 | Li et al. |
| 7,630,453 B2 * | 12/2009 | Noda ............................ 375/295 |
| 7,697,326 B2 | 4/2010 | Sommer et al. |
| 7,706,182 B2 | 4/2010 | Shalvi et al. |
| 7,716,538 B2 | 5/2010 | Gonzalez et al. |
| 7,804,718 B2 | 9/2010 | Kim |
| 7,805,663 B2 | 9/2010 | Brandman et al. |
| 7,805,664 B1 | 9/2010 | Yang et al. |
| 7,844,877 B2 | 11/2010 | Litsyn et al. |
| 7,911,848 B2 | 3/2011 | Eun et al. |
| 7,961,797 B1 | 6/2011 | Yang et al. |
| 7,975,192 B2 | 7/2011 | Sommer et al. |
| 8,020,073 B2 | 9/2011 | Emma et al. |
| 8,108,590 B2 | 1/2012 | Chow et al. |
| 8,122,328 B2 | 2/2012 | Liu et al. |
| 8,159,881 B2 | 4/2012 | Yang |
| 8,190,961 B1 | 5/2012 | Yang et al. |
| 8,250,324 B2 | 8/2012 | Haas et al. |
| 8,300,823 B2 | 10/2012 | Bojinov et al. |
| 8,305,812 B2 | 11/2012 | Levy et al. |
| 8,327,246 B2 | 12/2012 | Weingarten et al. |
| 8,407,560 B2 | 3/2013 | Ordentlich et al. |
| 8,417,893 B2 | 4/2013 | Khmelnitsky et al. |
| 2001/0034815 A1 | 10/2001 | Dugan et al. |
| 2002/0063774 A1 | 5/2002 | Hillis et al. |
| 2002/0085419 A1 | 7/2002 | Kwon et al. |
| 2002/0154769 A1 | 10/2002 | Petersen et al. |
| 2002/0156988 A1 | 10/2002 | Toyama et al. |
| 2002/0174156 A1 | 11/2002 | Birru et al. |
| 2003/0014582 A1 | 1/2003 | Nakanishi |
| 2003/0065876 A1 | 4/2003 | Lasser |
| 2003/0101404 A1 | 5/2003 | Zhao et al. |
| 2003/0105620 A1 | 6/2003 | Bowen |
| 2003/0177300 A1 | 9/2003 | Lee et al. |
| 2003/0192007 A1 | 10/2003 | Miller et al. |
| 2004/0015771 A1 | 1/2004 | Lasser et al. |
| 2004/0030971 A1 | 2/2004 | Tanaka et al. |
| 2004/0059768 A1 | 3/2004 | Denk et al. |
| 2004/0080985 A1 | 4/2004 | Chang et al. |
| 2004/0153722 A1 | 8/2004 | Lee |
| 2004/0153817 A1 | 8/2004 | Norman et al. |
| 2004/0181735 A1 | 9/2004 | Xin |
| 2004/0203591 A1 | 10/2004 | Lee |
| 2004/0210706 A1 | 10/2004 | In et al. |
| 2005/0013165 A1 | 1/2005 | Ban |
| 2005/0018482 A1 | 1/2005 | Cemea et al. |
| 2005/0083735 A1 | 4/2005 | Chen et al. |
| 2005/0117401 A1 | 6/2005 | Chen et al. |
| 2005/0120265 A1 | 6/2005 | Pline et al. |
| 2005/0128811 A1 | 6/2005 | Kato et al. |
| 2005/0138533 A1 | 6/2005 | Le-Bars et al. |
| 2005/0144213 A1 | 6/2005 | Simkins et al. |
| 2005/0144368 A1 | 6/2005 | Chung et al. |
| 2005/0169057 A1 | 8/2005 | Shibata et al. |
| 2005/0172179 A1 | 8/2005 | Brandenberger et al. |
| 2005/0213393 A1 | 9/2005 | Lasser |
| 2005/0243626 A1 | 11/2005 | Ronen |
| 2006/0059406 A1 | 3/2006 | Micheloni et al. |
| 2006/0059409 A1 | 3/2006 | Lee |
| 2006/0064537 A1 | 3/2006 | Oshima et al. |
| 2006/0101193 A1 | 5/2006 | Murin |
| 2006/0195651 A1 | 8/2006 | Estakhri et al. |
| 2006/0203587 A1 | 9/2006 | Li et al. |
| 2006/0221692 A1 | 10/2006 | Chen |
| 2006/0248434 A1 | 11/2006 | Radke et al. |
| 2006/0268608 A1 | 11/2006 | Noguchi et al. |
| 2006/0282411 A1 | 12/2006 | Fagin et al. |
| 2006/0284244 A1 | 12/2006 | Forbes et al. |
| 2006/0294312 A1 | 12/2006 | Walmsley |
| 2007/0025157 A1 | 2/2007 | Wan et al. |
| 2007/0063180 A1 | 3/2007 | Asano et al. |
| 2007/0081388 A1 | 4/2007 | Joo |

(56) References Cited

U.S. PATENT DOCUMENTS

| | | | |
|---|---|---|---|
| 2007/0098069 A1 | 5/2007 | Gordon | |
| 2007/0103992 A1 | 5/2007 | Sakui et al. | |
| 2007/0104004 A1 | 5/2007 | So et al. | |
| 2007/0109858 A1 | 5/2007 | Conley et al. | |
| 2007/0124652 A1 | 5/2007 | Litsyn et al. | |
| 2007/0140006 A1 | 6/2007 | Chen et al. | |
| 2007/0143561 A1 | 6/2007 | Gorobets | |
| 2007/0150694 A1 | 6/2007 | Chang et al. | |
| 2007/0168625 A1 | 7/2007 | Cornwell et al. | |
| 2007/0171714 A1 | 7/2007 | Wu et al. | |
| 2007/0171730 A1* | 7/2007 | Ramamoorthy et al. | 365/185.33 |
| 2007/0180346 A1 | 8/2007 | Murin | |
| 2007/0223277 A1 | 9/2007 | Tanaka et al. | |
| 2007/0226582 A1 | 9/2007 | Tang et al. | |
| 2007/0226592 A1* | 9/2007 | Radke | 714/766 |
| 2007/0228449 A1 | 10/2007 | Takano et al. | |
| 2007/0253249 A1 | 11/2007 | Kang et al. | |
| 2007/0253250 A1 | 11/2007 | Shibata et al. | |
| 2007/0263439 A1 | 11/2007 | Cornwell et al. | |
| 2007/0266291 A1 | 11/2007 | Toda et al. | |
| 2007/0271494 A1* | 11/2007 | Gorobets | 714/763 |
| 2007/0297226 A1 | 12/2007 | Mokhlesi | |
| 2008/0010581 A1 | 1/2008 | Alrod et al. | |
| 2008/0028014 A1 | 1/2008 | Hilt et al. | |
| 2008/0049497 A1 | 2/2008 | Mo | |
| 2008/0055989 A1 | 3/2008 | Lee et al. | |
| 2008/0082897 A1 | 4/2008 | Brandman et al. | |
| 2008/0092026 A1 | 4/2008 | Brandman et al. | |
| 2008/0104309 A1 | 5/2008 | Cheon et al. | |
| 2008/0112238 A1 | 5/2008 | Kim et al. | |
| 2008/0116509 A1 | 5/2008 | Harari et al. | |
| 2008/0126686 A1 | 5/2008 | Sokolov et al. | |
| 2008/0127104 A1 | 5/2008 | Li et al. | |
| 2008/0128790 A1 | 6/2008 | Jung | |
| 2008/0130341 A1 | 6/2008 | Shalvi et al. | |
| 2008/0137413 A1 | 6/2008 | Kong et al. | |
| 2008/0137414 A1 | 6/2008 | Park et al. | |
| 2008/0141043 A1 | 6/2008 | Flynn et al. | |
| 2008/0148115 A1 | 6/2008 | Sokolov et al. | |
| 2008/0158958 A1 | 7/2008 | Shalvi et al. | |
| 2008/0159059 A1 | 7/2008 | Moyer | |
| 2008/0162079 A1 | 7/2008 | Astigarraga et al. | |
| 2008/0168216 A1 | 7/2008 | Lee | |
| 2008/0168320 A1 | 7/2008 | Cassuto et al. | |
| 2008/0181001 A1 | 7/2008 | Shalvi | |
| 2008/0198650 A1 | 8/2008 | Shalvi et al. | |
| 2008/0198652 A1 | 8/2008 | Shalvi et al. | |
| 2008/0201620 A1 | 8/2008 | Gollub | |
| 2008/0209114 A1 | 8/2008 | Chow et al. | |
| 2008/0219050 A1 | 9/2008 | Shalvi et al. | |
| 2008/0225599 A1 | 9/2008 | Chae | |
| 2008/0250195 A1 | 10/2008 | Chow et al. | |
| 2008/0263262 A1 | 10/2008 | Sokolov et al. | |
| 2008/0282106 A1 | 11/2008 | Shalvi et al. | |
| 2008/0285351 A1 | 11/2008 | Shlick et al. | |
| 2008/0301532 A1 | 12/2008 | Uchikawa et al. | |
| 2009/0024905 A1 | 1/2009 | Shalvi et al. | |
| 2009/0027961 A1 | 1/2009 | Park et al. | |
| 2009/0043951 A1 | 2/2009 | Shalvi et al. | |
| 2009/0046507 A1 | 2/2009 | Aritome | |
| 2009/0072303 A9 | 3/2009 | Prall et al. | |
| 2009/0091979 A1 | 4/2009 | Shalvi | |
| 2009/0103358 A1 | 4/2009 | Sommer et al. | |
| 2009/0106485 A1 | 4/2009 | Anholt | |
| 2009/0113275 A1 | 4/2009 | Chen et al. | |
| 2009/0125671 A1 | 5/2009 | Flynn et al. | |
| 2009/0132755 A1 | 5/2009 | Radke | |
| 2009/0132895 A1* | 5/2009 | Jiang et al. | 714/781 |
| 2009/0144598 A1 | 6/2009 | Yoon et al. | |
| 2009/0144600 A1 | 6/2009 | Perlmutter et al. | |
| 2009/0150599 A1 | 6/2009 | Bennett | |
| 2009/0150748 A1 | 6/2009 | Egner et al. | |
| 2009/0157964 A1 | 6/2009 | Kasorla et al. | |
| 2009/0158126 A1 | 6/2009 | Perlmutter et al. | |
| 2009/0168524 A1 | 7/2009 | Golov et al. | |
| 2009/0187803 A1 | 7/2009 | Anholt et al. | |
| 2009/0199074 A1 | 8/2009 | Sommer | |
| 2009/0213653 A1 | 8/2009 | Perlmutter et al. | |
| 2009/0213654 A1 | 8/2009 | Perlmutter et al. | |
| 2009/0228761 A1 | 9/2009 | Perlmutter et al. | |
| 2009/0240872 A1 | 9/2009 | Perlmutter et al. | |
| 2009/0282185 A1 | 11/2009 | Van Cauwenbergh | |
| 2009/0282186 A1 | 11/2009 | Mokhlesi et al. | |
| 2009/0287930 A1 | 11/2009 | Nagaraja | |
| 2009/0300269 A1 | 12/2009 | Radke et al. | |
| 2009/0323942 A1 | 12/2009 | Sharon et al. | |
| 2010/0005270 A1 | 1/2010 | Jiang | |
| 2010/0025811 A1 | 2/2010 | Bronner et al. | |
| 2010/0030944 A1 | 2/2010 | Hinz | |
| 2010/0058146 A1 | 3/2010 | Weingarten et al. | |
| 2010/0064096 A1 | 3/2010 | Weingarten et al. | |
| 2010/0088557 A1 | 4/2010 | Weingarten et al. | |
| 2010/0091535 A1 | 4/2010 | Sommer et al. | |
| 2010/0095186 A1 | 4/2010 | Weingarten | |
| 2010/0110787 A1 | 5/2010 | Shalvi et al. | |
| 2010/0115376 A1 | 5/2010 | Shalvi et al. | |
| 2010/0122113 A1 | 5/2010 | Weingarten et al. | |
| 2010/0124088 A1 | 5/2010 | Shalvi et al. | |
| 2010/0131580 A1 | 5/2010 | Kanter et al. | |
| 2010/0131806 A1 | 5/2010 | Weingarten et al. | |
| 2010/0131809 A1 | 5/2010 | Katz | |
| 2010/0131826 A1 | 5/2010 | Shalvi et al. | |
| 2010/0131827 A1 | 5/2010 | Sokolov et al. | |
| 2010/0131831 A1 | 5/2010 | Weingarten et al. | |
| 2010/0146191 A1 | 6/2010 | Katz | |
| 2010/0146192 A1 | 6/2010 | Weingarten et al. | |
| 2010/0149881 A1 | 6/2010 | Lee et al. | |
| 2010/0172179 A1 | 7/2010 | Gorobets et al. | |
| 2010/0174853 A1 | 7/2010 | Lee et al. | |
| 2010/0180073 A1 | 7/2010 | Weingarten et al. | |
| 2010/0199149 A1 | 8/2010 | Weingarten et al. | |
| 2010/0211724 A1 | 8/2010 | Weingarten | |
| 2010/0211833 A1 | 8/2010 | Weingarten | |
| 2010/0211856 A1 | 8/2010 | Weingarten | |
| 2010/0241793 A1 | 9/2010 | Sugimoto et al. | |
| 2010/0246265 A1 | 9/2010 | Moschiano et al. | |
| 2010/0251066 A1 | 9/2010 | Radke | |
| 2010/0253555 A1 | 10/2010 | Weingarten et al. | |
| 2010/0257309 A1 | 10/2010 | Barsky et al. | |
| 2010/0269008 A1 | 10/2010 | Leggette et al. | |
| 2010/0293321 A1 | 11/2010 | Weingarten | |
| 2010/0318724 A1 | 12/2010 | Yeh | |
| 2011/0051521 A1 | 3/2011 | Levy et al. | |
| 2011/0055461 A1 | 3/2011 | Steiner et al. | |
| 2011/0093650 A1 | 4/2011 | Kwon et al. | |
| 2011/0096612 A1 | 4/2011 | Steiner et al. | |
| 2011/0099460 A1 | 4/2011 | Dusija et al. | |
| 2011/0119562 A1 | 5/2011 | Steiner et al. | |
| 2011/0153919 A1 | 6/2011 | Sabbag | |
| 2011/0161775 A1 | 6/2011 | Weingarten | |
| 2011/0194353 A1 | 8/2011 | Hwang et al. | |
| 2011/0209028 A1 | 8/2011 | Post et al. | |
| 2011/0214029 A1 | 9/2011 | Steiner et al. | |
| 2011/0214039 A1 | 9/2011 | Steiner et al. | |
| 2011/0246792 A1 | 10/2011 | Weingarten | |
| 2011/0246852 A1 | 10/2011 | Sabbag | |
| 2011/0252187 A1 | 10/2011 | Segal et al. | |
| 2011/0252188 A1 | 10/2011 | Weingarten | |
| 2011/0271043 A1 | 11/2011 | Segal et al. | |
| 2011/0302428 A1 | 12/2011 | Weingarten | |
| 2012/0001778 A1 | 1/2012 | Steiner et al. | |
| 2012/0005554 A1 | 1/2012 | Steiner et al. | |
| 2012/0005558 A1 | 1/2012 | Steiner et al. | |
| 2012/0005560 A1 | 1/2012 | Steiner et al. | |
| 2012/0008401 A1 | 1/2012 | Katz et al. | |
| 2012/0008414 A1 | 1/2012 | Katz et al. | |
| 2012/0017136 A1 | 1/2012 | Ordentlich et al. | |
| 2012/0051144 A1 | 3/2012 | Weingarten et al. | |
| 2012/0063227 A1 | 3/2012 | Weingarten et al. | |
| 2012/0066441 A1 | 3/2012 | Weingarten | |
| 2012/0110250 A1 | 5/2012 | Sabbag et al. | |
| 2012/0124273 A1 | 5/2012 | Goss et al. | |
| 2012/0246391 A1 | 9/2012 | Meir et al. | |

(56) References Cited

OTHER PUBLICATIONS

Search Report of PCT Patent Application WO 2009/095902 A3, Mar. 4, 2010.
Search Report of PCT Patent Application WO 2009/078006 A3, Mar. 4, 2010.
Search Report of PCT Patent Application WO 2009/074979 A3, Mar. 4, 2010.
Search Report of PCT Patent Application WO 2009/074978 A3, Mar. 4, 2010.
Search Report of PCT Patent Application WO 2009/072105 A3, Mar. 4, 2010.
Search Report of PCT Patent Application WO 2009/072104 A3, Mar. 4, 2010.
Search Report of PCT Patent Application WO 2009/072103 A3, Mar. 4, 2010.
Search Report of PCT Patent Application WO 2009/072102 A3, Mar. 4, 2010.
Search Report of PCT Patent Application WO 2009/072101 A3, Mar. 4, 2010.
Search Report of PCT Patent Application WO 2009/072100 A3, Mar. 4, 2010.
Search Report of PCT Patent Application WO 2009/053963 A3, Mar. 4, 2010.
Search Report of PCT Patent Application WO 2009/053962 A3, Mar. 4, 2010.
Search Report of PCT Patent Application WO 2009/053961 A3, Mar. 4, 2010.
Search Report of PCT Patent Application WO 2009/037697 A3, Mar. 4, 2010.
Yani Chen, Keshab K. Parhi, "Small Area Parallel Chien Search Architectures for Long BCH Codes", Ieee Transactions on Very Large Scale Integration(VLSI) Systems, vol. 12, No. 5, May 2004.
Yuejian Wu, "Low Power Decoding of BCH Codes", Nortel Networks, Ottawa, Ont., Canada, in Circuits and systems, 2004. ISCAS '04. Proceeding of the 2004 International Symposium on Circuits and Systems, published May 23-26, 2004, vol. 2, pp. 11-369-72 vol. 2.
Michael Purser, "Introduction to Error Correcting Codes", Artech House Inc., 1995.
Ron M. Roth, "Introduction to Coding Theory", Cambridge University Press, 2006.
Akash Kumar, Sergei Sawitzki, "High-Throughput and Low Power Architectures for Reed Solomon Decoder", (a.kumar at tue.nl, Eindhoven University of Technology and sergei.sawitzki at philips. com), Oct. 2005.
Todd K.Moon, "Error Correction Coding Mathematical Methods and Algorithms", A John Wiley & Sons, Inc., 2005.
Richard E. Blahut, "Algebraic Codes for Data Transmission", Cambridge University Press, 2003.
David Esseni, Bruno Ricco, "Trading-Off Programming Speed and Current Absorption in Flash Memories with the Ramped-Gate Programming Technique", Ieee Transactions on Electron Devices, vol. 47, No. 4, Apr. 2000.
Giovanni Campardo, Rino Micheloni, David Novosel, "VLSI-Design of Non-Volatile Memories", Springer Berlin Heidelberg New York, 2005.
John G. Proakis, "Digital Communications", 3rd ed., New York: McGraw-Hill, 1995.
J.M. Portal, H. Aziza, D. Nee, "EEPROM Memory: Threshold Voltage Built in Self Diagnosis", ITC International Test Conference, Paper 2.1, Feb. 2005.
J.M. Portal, H. Aziza, D. Nee, "EEPROM Diagnosis Based on Threshold Voltage Embedded Measurement", Journal of Electronic Testing: Theory and Applications 21, 33-42, 2005.
G. Tao, A. Scarpa, J. Dijkstra, W. Stidl, F. Kuper, "Data retention prediction for modern floating gate non-volatile memories", Microelectronics Reliability 40 (2000), 1561-1566.
T. Hirncno, N. Matsukawa, H. Hazama, K. Sakui, M. Oshikiri, K. Masuda, K. Kanda, Y. Itoh, J. Miyamoto, "A New Technique for Measuring Threshold Voltage Distribution in Flash EEPROM Devices", Proc. IEEE 1995 Int. Conference on Microelectronics Test Structures, vol. 8, Mar. 1995.
Boaz Eitan, Guy Cohen, Assaf Shappir, Eli Lusky, Amichai Givant, Meir Janai, Ilan Bloom, Yan Polansky, Oleg Dadashev, Avi Lavan, Ran Sahar, Eduardo Maayan, "4-bit per Cell NROM Reliability", Appears on the website of Saifun.com, 2005.
Paulo Cappelletti, Clara Golla, Piero Olivo, Enrico Zanoni, "Flash Memories", Kluwer Academic Publishers, 1999.
Jedec Standard, "Stress-Test-Driven Qualification of Integrated Circuits", JEDEC Solid State Technology Association. JEDEC Standard No. 47F pp. 1-26, Dec. 2007.
Dempster, et al., "Maximum Likelihood from Incomplete Data via the EM Algorithm", Journal of the Royal Statistical Society. Series B (Methodological), vol. 39, No. 1 (1997), pp. 1-38.
Mielke, et al., "Flash EEPROM Threshold Instabilities due to Charge Trapping During Program/Erase Cycling", IEEE Transactions on Device and Materials Reliability, vol. 4, No. 3, Sep. 2004, pp. 335-344.
Daneshbeh, "Bit Serial Systolic Architectures for Multiplicative Inversion and Division over GF (2)", A thesis presented to the University of Waterloo, Ontario, Canada, 2005, pp. 1-118.
Chen, Formulas for the solutions of Quadratic Equations over GF (2), IEEE Trans. Inform. Theory, vol. IT-28, No. 5, Sep. 1982, pp. 792-794.
Berlekamp et al., "On the Solution of Algebraic Equations over Finite Fields", Inform. Cont. 10, Oct. 1967, pp. 553-564.

\* cited by examiner

| Subsequence | 000 | 001 | 010 | 011 | 100 | 101 | 110 | 111 |
|---|---|---|---|---|---|---|---|---|
| Symbol | 0 | 1 | 2 | 3 | 4 | 5 | 6 | 7 |

| Subsequence | 111 | 110 | 100 | 101 | 001 | 000 | 010 | 011 |
|---|---|---|---|---|---|---|---|---|
| Symbol | 0 | 1 | 2 | 3 | 4 | 5 | 6 | 7 |

1100 — Z = the number represented by the r bits

1110 — Counter = 1

1120 — Repeat $\lceil \frac{r}{\log_2 L} \rceil$ times

1130 — $Symbol_{counter}$ = remainder of the division of Z by L

1140 — Counter = Counter + 1

1150 — Z = the quotient of the division of Z by L

1160 — End of loop

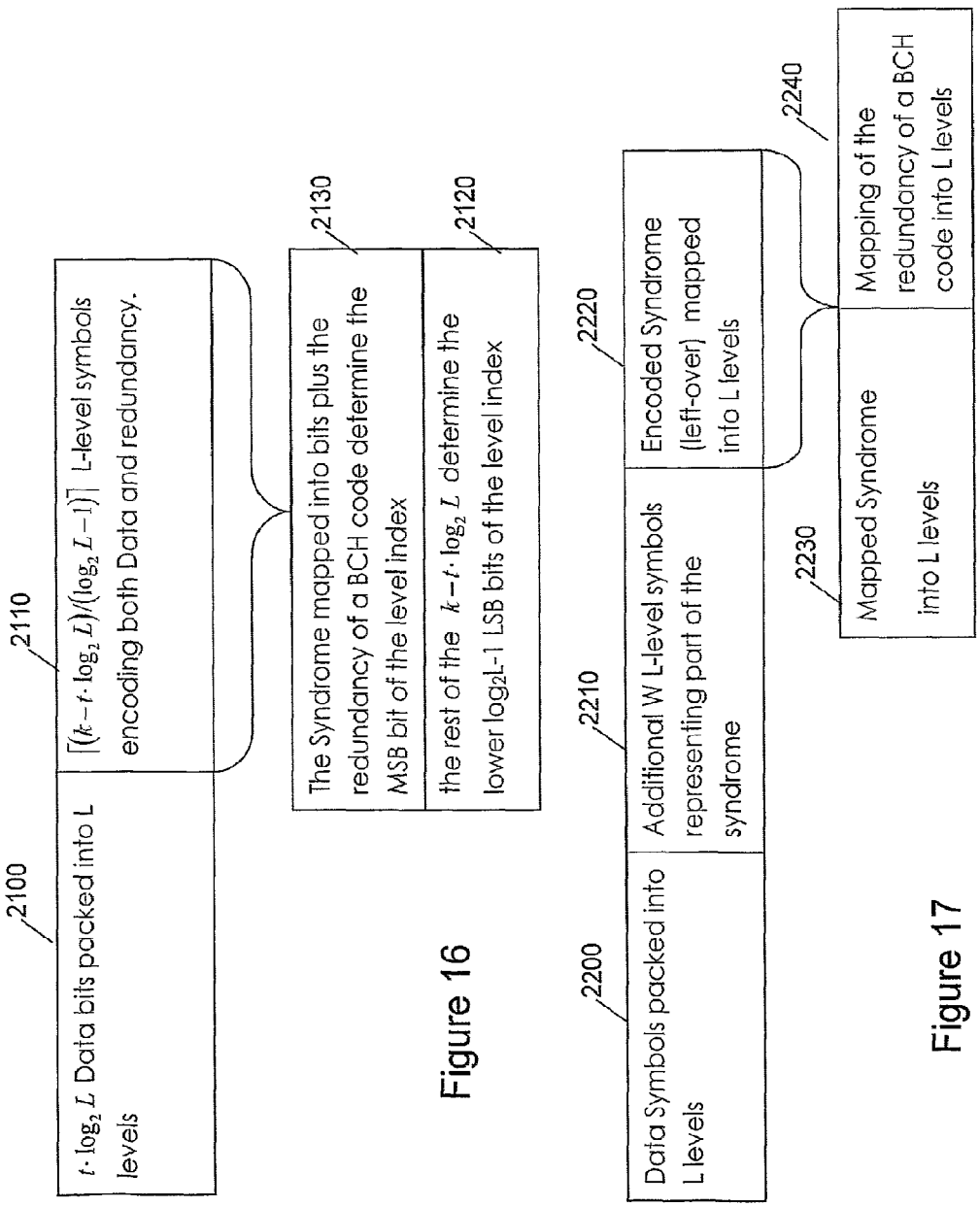

SYSTEMS AND METHODS FOR ERROR CORRECTION AND DECODING ON MULTI-LEVEL PHYSICAL MEDIA

CROSS REFERENCE TO RELATED APPLICATIONS

This application is a continuation and claims priority of U.S. application Ser. No. 12/667,043, filed on 29 Dec. 2009, now U.S. Pat. No. 8,359,516, which claims the benefit of the National Phase Application of PCT International Application No. PCT/IL2008/001229, International Filing Date Sep. 17, 2008, published on Jun. 18, 2009 as International Publication No. WO 2009/074978, which in turn claims priority from U.S. Provisional Patent Application No. 61/006,385, filed Jan. 10, 2008 and entitled "A System for Error Correction Encoder and Decoder Using the Lee Metric and Adapted to Work on Multi-Level Physical Medial", U.S. Provisional Patent Application No. 61/064,995, filed Apr. 8, 2008 and entitled "Systems and Methods for Error Correction and Decoding on Multi-Level Physical Media", U.S. Provisional Patent Application No. 60/996,948, filed Dec. 12, 2007 and entitled "Low Power BCH/RS Decoding: a Low Power Chien-Search Implementation", U.S. Provisional Patent Application No. 61/071,487, filed May 1, 2008 and entitled "Chien-Search System Employing a Clock-Gating Scheme to Save Power for Error Correction Decoder and other Applications" and U.S. Provisional Patent Application No. 61/071,468, filed Apr. 30, 2008 and entitled "A Low Power Chien-Search Based BCH/RS Recoding System for Flash Memory, Mobile Communications Devices and Other Applications", the disclosures of which are expressly incorporated by reference herein in their entireties.

Other co-pending applications include: U.S. Provisional Application No. 60/960,207, filed Sep. 20, 2007 and entitled "Systems and Methods for Coupling Detection in Flash Memory", U.S. Provisional Application No. 61/071,467, filed Apr. 30, 2008 and entitled "Improved Systems and Methods for Determining Logical Values of Coupled Flash Memory Cells", U.S. Provisional Application No. 60/960,943, filed Oct. 22, 2007 and entitled "Systems and methods to reduce errors in Solid State Disks and Large Flash Devices" and U.S. Provisional Application No. 61/071,469, filed Apr. 30, 2008 and entitled "Systems and Methods for Averaging Error Rates in Non-Volatile Devices and Storage Systems", U.S. Provisional Application No. 60/996,027, filed Oct. 25, 2007 and entitled "Systems and Methods for Coping with Variable Bit Error Rates in Flash Devices", U.S. Provisional Application No. 61/071,466, filed Apr. 30, 2008 and entitled "Systems and Methods for Multiple Coding Rates in Flash Devices", U.S. Provisional Application No. 61/006,120, filed Dec. 19, 2007 and entitled "Systems and Methods for Coping with Multi Stage Decoding in Flash Devices", U.S. Provisional Application No. 61/071,464, filed Apr. 30, 2008 and entitled "A Decoder Operative to Effect A Plurality of Decoding Stages Upon Flash Memory Data and Methods Useful in Conjunction Therewith", U.S. Provisional Application No. 60/996,782, filed Dec. 5, 2007 and entitled "Systems and Methods for Using a Training Sequence in Flash Memory", U.S. Provisional Application No. 61/064,853, filed Mar. 31, 2008 and entitled "Flash Memory Device with Physical Cell Value Deterioration Accommodation and Methods Useful in Conjunction Therewith", U.S. Provisional Application No. 61/129,608, filed Jul. 8, 2008 and entitled "A Method for Acquiring and Tracking Detection Thresholds in Flash Devices", U.S. Provisional Application No. 61/006,806, filed Jan. 31, 2008 and entitled "Systems and Methods for using a Erasure Coding in Flash memory", U.S. Provisional Application No. 61/071,486, filed May 1, 2008 and entitled "Systems and Methods for Handling Immediate Data Errors in Flash Memory", U.S. Provisional Application No. 61/006,078, filed Dec. 18, 2007 and entitled "Systems and Methods for Multi Rate Coding in Multi Level Flash Devices", U.S. Provisional Application No. 61/064,923, filed Apr. 30, 2008 and entitled "Apparatus For Coding At A Plurality Of Rates In Multi-Level Flash Memory Systems, And Methods Useful In Conjunction Therewith", U.S. Provisional Application No. 61/006,805, filed Jan. 31, 2008 and entitled "A Method for Extending the Life of Flash Devices", U.S. Provisional Application No. 61/071,465, filed Apr. 30, 2008 and entitled "Systems and Methods for Temporarily Retiring Memory Portions", U.S. Provisional Application No. 61/064,760, filed Mar. 25, 2008 and entitled "Hardware efficient implementation of rounding in fixed-point arithmetic", U.S. Provisional Application No. 61/071,404, filed Apr. 28, 2008 and entitled "Apparatus and Methods for Hardware-Efficient Unbiased Rounding", U.S. Provisional Application No. 61/136,234, filed Aug. 20, 2008 and entitled "A Method Of Reprogramming A Non-Volatile Memory Device Without Performing An Erase Operation", U.S. Provisional Application No. 61/129,414, filed Jun. 25, 2008 and entitled "Improved Programming Speed in Flash Devices Using Adaptive Programming", and several other co-pending patent applications being filed concurrently (same day).

FIELD OF THE INVENTION

The present invention relates generally to error correction encoding and decoding and more particularly to encoding and decoding in flash memory systems.

BACKGROUND OF THE INVENTION

Many types of flash memory are known. Conventional flash memory technology is described in the following publications inter alia:

Paulo Cappelletti, Clara Golla, Piero Olivo, Enrico Zanoni, "Flash Memories", Kluwer Academic Publishers, 1999

G. Campardo, R. Micheloni, D. Novosel, "CLSI-Design of Non-Volatile Memories", Springer Berlin Heidelberg New York, 2005

The Lee metric is a known metric-based error correction encoder/decoder functionality.

Prior art technologies related to the present invention include:

[1] "Error Correction Coding Mathematical Methods and Algorithms", Todd K. Moon, A JOHN WILEY & SONS, INC., 2005.

[2] "Introduction to Coding Theory", Ron M. Roth, Cambridge University Press, 2006.

[3] "Algebraic Codes for Data Transmission", Richard E. Blahut, Cambridge University Press, 2003.

References to square-bracketed numbers in the specification refer to the above documents.

The disclosures of all publications and patent documents mentioned in the specification, and of the publications and patent documents cited therein directly or indirectly, are hereby incorporated by reference.

SUMMARY OF THE INVENTION

The following terms may be construed either in accordance with any definition thereof appearing in the prior art literature or in accordance with the specification, or as follows:

Bit error rate (BER): a parameter that a flash memory device manufacturer commits to vis a vis its customers, expressing the maximum proportion of wrongly read bits (wrongly read bits/total number of bits) that users of the flash memory device need to expect at any time during the stipulated lifetime of the flash memory device e.g. 10 years.

Block: a set of flash memory device cells which must, due to physical limitations of the flash memory device, be erased together. Also termed erase sector, erase block.

Cell: A component of flash memory that stores one bit of information (in single-level cell devices) or n bits of information (in a multi-level device having 2 exp n levels). Typically, each cell comprises a floating-gate transistor. n may or may not be an integer. "Multi-level" means that the physical levels in the cell are, to an acceptable level of certainty, statistically partionable into multiple distinguishable regions, plus a region corresponding to zero, such that digital values each comprising multiple bits can be represented by the cell. In contrast, in single-level cells, the physical levels in the cell are assumed to be statistically partitionable into only two regions, one corresponding to zero and one other, non-zero region, such that only one bit can be represented by a single-level cell.

Charge level: the measured voltage of a cell which reflects its electric charge.

Cycling: Repeatedly writing new data into flash memory cells and repeatedly erasing the cells between each two writing operations.

Decision regions: Regions extending between adjacent decision levels, e.g. if decision levels are 0, 2 and 4 volts respectively, the decision regions are under 0 V, 0 V-2 V, 2V-4 V, and over 4 V.

Demapping: basic cell-level reading function in which a digital n-tuple originally received from an outside application is derived from a physical value representing a physical state in the cell having a predetermined correspondence to the digital n-tuple.

Digital value or "logical value": n-tuple of bits represented by a cell in flash memory an capable of generating 2 exp n distinguishable levels of a typically continuous physical value such as charge, where n may or may not be an integer.

Erase cycle: The relatively slow process of erasing a block of cells (erase sector), each block typically comprising more than one page, or, in certain non-flash memory devices, of erasing a single cell or the duration of so doing. An advantage of erasing cells collectively in blocks as in flash memory, rather than individually, is enhanced programming speed: Many cells and typically even many pages of cells are erased in a single erase cycle.

Erase-write cycle: The process of erasing a block of cells (erase sector), each block typically comprising a plurality of pages, and subsequently writing new data into at least some of them. The terms "program" and "write" are used herein generally interchangeably.

Flash memory: Non-volatile computer memory including cells that are erased block by block, each block typically comprising more than one page, but are written into and read from, page by page. Includes NOR-type flash memory, NAND-type flash memory, and PRAM, e.g. Samsung PRAM, inter glia, and flash memory devices with any suitable number of levels per cell, such as but not limited to 2, 4, or 8.

Mapping: basic cell-level writing function in which incoming digital n-tuple is mapped to a program level by inducing a program level in the cell, having a predetermined correspondence to the incoming logical value.

Page: A portion, typically 512 or 2048 or 4096 bytes in size, of a flash memory e.g. a NAND or NOR flash memory device. Writing can be performed page by page, as opposed to erasing which can be performed only erase sector by erase sector. A few bytes, typically 16-32 for every 512 data bytes are associated with each page (typically 16, 64 or 128 per page), for storage of error correction information. A typical block may include 32 512-byte pages or 64 2048-byte pages.

Precise read, soft read: Cell threshold voltages are read at a precision (number of bits) greater than the number of Mapping levels ($2^n$). The terms precise read or soft read are interchangeable. In contrast, in "hard read", cell threshold voltages are read at a precision (number of bits) smaller than the number of Mapping levels ($2^n$ where n=number of bits per cell).

Present level, Charge level: The amount of charge in the cell. The Amount of charge currently existing in a cell, at the present time, as opposed to "program level", the amount of charge originally induced in the cell (i.e. at the end of programming)

Program: same as "write".

Program level (programmed level, programming level): amount of charge originally induced in a cell to represent a given logical value, as opposed to "present level".

Reprogrammability (Np): An aspect of flash memory quality. This is typically operationalized by a reprogrammability parameter, also termed herein "Np", denoting the number of times that a flash memory can be re-programmed (number of erase-write cycles that the device can withstand) before the level of errors is so high as to make an unacceptably high proportion of those errors irrecoverable given a predetermined amount of memory devoted to redundancy. Typically recoverability is investigated following a conventional aging simulation process which simulates or approximates the data degradation effect that a predetermined time period e.g. a 10 year period has on the flash memory device, in an attempt to accommodate for a period of up to 10 years between writing of data in flash memory and reading of the data therefrom.

Resolution: Number of levels in each cell, which in turn determines the number of bits the cell can store; typically a cell with $2^n$ levels stores n bits. Low resolution (partitioning the window, W, of physical values a cell can assume into a small rather than large number of levels per cell) provides high reliability.

Retention: of original physical levels induced in the cells; retention is typically below 100% resulting in deterioration of original physical levels into present levels.

Retention time: The amount of time that data has been stored in a flash device, typically without, or substantially without, voltage having been supplied to the flash device i.e. the time which elapses between programming of a page and reading of the same page.

Symbol: Logical value

Threshold level: the voltage (e.g.) against which the charge level of a cell is measured. For example, a cell may be said to store a particular digital n-tuple D if the charge level or other physical level of the cell falls between two threshold values T.

Certain embodiments of the present invention seek to provide improved methods for error correction encoding and decoding, for flash memory and other applications.

Reed Solomon (RS) codes are common error correction codes (ECC) used in various applications such as storage and probably among the most prevalent codes today. These codes are particularly common when the output from the physical media is binary and there is no additional information regarding the reliability of the bits. In some cases these codes are also used to handle the case of erasures—i.e. bits whose value is unknown.

Many of these codes are systematic. That is, the code may be divided into two sections, the first containing the original data and the second containing spare bits, containing redundant information which allows a decoder to reconstruct the original data if errors have occurred in the first and/or second sections. The number of errors that can be corrected is a function of the code length and of the length of the redundancy within the code.

In RS codes, the data sequence is a bit sequence which is divided into subsets called symbols. The code itself is a sequence of symbols and only symbols are corrected. It is irrelevant which bit or if several bits (say f, the number of bits in a symbol) were in error in a symbol; the symbol is corrected as a unit. The code t has a limit on the number of symbols that can be corrected regardless of how many bits were corrected. That is, an RS code can correct all received sequences as long as their Hamming distance from the original codeword is not larger than a certain value given by D/2, where "Hamming distance" between two sequences of symbols is the count of a number of different symbols between the sequences. D is also equal to the number of symbols in the redundancy section of the code; therefore, the redundancy would have D*f bits. A special case of RS codes are binary BCH codes, also known as alternant codes. These codes may be viewed as a subset of RS codes where only those code-words whose symbols are only 0 and 1 are used. With these codes it is possible to correct up to D errors with a redundancy of D*f bits. f is now chosen such that the overall length of the code (n) is smaller than n<2f. The code corrects sequences as long as their Hamming distance is less than or equal to D, where the Hamming distance is taken over bits.

Certain embodiments of the present invention seek to provide a code which outperforms the binary BCH code for certain applications e.g. those in which short bit sequences are mapped to different levels—such as, for example, in multi-level Flash memory devices where every 2-4 bits are mapped to 4-16 levels.

Prior art FIG. 1 illustrates the distribution of the charge level in a 2 bit/cell Flash device. Every 2 bits are mapped into one of the 4 levels in each cell. Errors may occur if one charge level is read as another. Almost all errors occur when one level is mistaken for an adjacent level. Only rarely do errors occur between non-adjacent levels.

If a binary BCH code is used, gray mapping of the levels into bits assists in reducing the number of bit error per programmed cell. However, the binary BCH code does not take into account the fact that more than one bit error per cell occurs only very rarely indeed.

There is thus provided, in accordance with at least one embodiment of the present invention, a method for error correction encoding of L level application data residing in a memory comprising L level Multi-level cells (MLCs) including at least some Multi-level cells (MLCs) in which the application data is residing and at least some Multi-level cells (MLCs) which are at least partly available to accept data other than the application data, the method comprising encoding the L level application data over a prime field thereby to generate non-binary redundancy data, binarizing at least some of the non-binary redundancy data thereby to generate binarized redundancy data, effecting binary error-correction encoding of the binarized redundancy data, thereby to generate binary redundancy data, combining the binarized redundancy data and the binary redundancy data thereby to generate combined binarized/binary redundancy data; and restoring the combined binarized/binary redundancy data to L level form, thereby to generate restored L level redundancy data, and storing the restored L level redundancy data in at least some of the at least partly available L level Multi-level cells (MLCs).

Further in accordance with at least one embodiment of the present invention, the method also comprises, for at least one L level MLC, utilizing less than L levels for storing at least a portion of the L level application data and utilizing remaining ones of the L levels for storing at least a portion of the combined binarized/binary redundancy data.

Still further in accordance with at least one embodiment of the present invention, binarizing comprises binarizing all of the non-binary redundancy data.

Additionally in accordance with at least one embodiment of the present invention, binarizing comprises binarizing only some of the non-binary redundancy data thereby to define a portion of the non-binary redundancy data which is un-binarized, and wherein the method also comprises L-level transforming the un-binarized non-binary redundancy data to L-level un-binarized non-binary redundancy data.

Still further in accordance with at least one embodiment of the present invention, binarizing and L-level transforming are effected by a single transform function.

Further in accordance with at least one embodiment of the present invention, the method also comprises storing the L-level un-binarized non-binary redundancy data in the L level Multi-level cells (MLCs).

Still further in accordance with at least one embodiment of the present invention, the encoding over a prime field comprises Reed-Solomon encoding over a prime field.

Still further in accordance with at least one embodiment of the present invention, the combining comprises concatenating the binarized redundancy data and the binary redundancy data thereby to generate concatenated binarized/binary redundancy data.

Additionally in accordance with at least one embodiment of the present invention, the binary error-correction encoding comprises BCH encoding of the binarized redundancy data, thereby to generate BCH-encoded redundancy data.

Further in accordance with at least one embodiment of the present invention, the at least some Multi-level cells (MLCs) which are at least partly available to accept data other than the application data comprise entirely available Multi-level cells (MLCs) in which no L level application data is residing, and wherein the storing comprises storing the restored L level redundancy data in at least some of the entirely available L level Multi-level cells (MLCs).

Also provided, in accordance with at least one embodiment of the present invention, is a method for error correction decoding of at least restored L level redundancy data residing in a memory comprising L level Multi-level cells (MLCs) including at least some Multi-level cells (MLCs) in which possibly erroneous L-level application data resides and at least some Multi-level cells (MLCs) which store at least the restored L level redundancy data, the method comprising binarizing the at least restored L level redundancy data, thereby to generate binarized restored L level redundancy data, deriving binary redundancy data from the binarized restored L level redundancy data, effecting binary error-correction decoding of the binary redundancy data, thereby to generate binarized redundancy data, transforming the binarized redundancy data to generate non-binary redundancy data, and decoding the non-binary redundancy data and the possibly erroneous L-level application data over a prime field, thereby to generate decoded L level application data.

Further in accordance with at least one embodiment of the present invention, binarizing comprises binarizing only some of the non-binary redundancy data thereby to define a portion of the non-binary redundancy data which is un-binarized, and wherein the method also comprises L-level transforming the un-binarized non-binary redundancy data to L-level un-binarized non-binary redundancy data.

Also provided, in accordance with at least one embodiment of the present invention, is an apparatus for error correction encoding of L level application data residing in a memory comprising L level Multi-level cells (MLCs) including at least some Multi-level cells (MLCs) in which the application data is residing and at least some Multi-level cells (MLCs) which are at least partly available to accept data other than the application data, the apparatus comprising prime-field encoding apparatus operative to encode the L level application data over a prime field thereby to generate non-binary redundancy data, binarization apparatus operative to binarize at least some of the non-binary redundancy data thereby to generate binarized redundancy data, binary ECC apparatus operative to effect binary error-correction encoding of the binarized redundancy data, thereby to generate binary redundancy data; and data combination apparatus operative to combine the binarized redundancy data and the binary redundancy data thereby to generate combined binarized/binary redundancy data, and L-level restoration apparatus operative to restore the combined binarized/binary redundancy data to L level form, thereby to generate restored L level redundancy data, and storing the restored L level redundancy data in at least some of the at least partly available L level Multi-level cells (MLCs).

Additionally provided, in accordance with at least one embodiment of the present invention, is a method for operating a flash device, the method comprising using Lee distance based codes in the flash device, thereby increasing the number of errors that can be corrected for a given number of redundancy cells compared with Hamming distance based codes.

Also provided, in accordance with at least one embodiment of the present invention, is a method for operating a flash device, the method comprising providing a Lee code associated with a first group of symbols; and coding data in the flash device using a second group of symbols, the second group being a sub group of the first group, so as to allow extending the number of errors that can be corrected for a given number of redundancy cells compared with Hamming distance based codes.

Further provided, in accordance with yet another embodiment of the present invention, is a method for operating a flash device, the method comprising providing a Lee code associated with a first group of symbols, coding data in the flash device using a second group of symbols, the second group being a sub group of the first group, giving rise to a first data stream, producing a redundancy data stream from the first data stream using a redundancy code, thereby increasing the number of errors that can be corrected for a given number of redundancy cells compared with Hamming distance based codes. Further in accordance with at least one embodiment of the present invention, the first data stream is associated with a first group of symbols and the redundancy data stream is associated with a second group of symbols, the second group being a sub group of the first group.

Further provided, in accordance with at least one embodiment of the present invention, is a decoding system comprising a Lee metric-based decoder operative to decode multi-level physical media.

Also provided, in accordance with at least one embodiment of the present invention, is a method for error correction comprising encoding and decoding, thereby to effect error correction and using a separate encoder to store a Syndrome computation to be used during the decoding.

Yet further provided, in accordance with at least one embodiment of the present invention, is a method for error correction comprising encoding and decoding, thereby to effect error correction, including encoding a syndrome; and encapsulating and mapping the encoded syndrome into designated media cells.

Also provided, in accordance with at least one embodiment of the present invention, is a method for error correction comprising encoding and decoding, thereby to effect error correction, including encoding a syndrome, and reducing error probability in the encoded Syndrome by encapsulating and mapping the encoded Syndrome mixed with data bits into designated media cells.

Also provided, in accordance with at least one embodiment of the present invention, is a method for error correction comprising encoding and decoding, thereby to effect error correction, including multiplying by an inverse matrix to achieve a reduced number of bits sufficient to encode the syndrome and encoding the syndrome using only the reduced number of bits.

Further in accordance with at least one embodiment of the present invention, the multi-level physical media includes media having less levels than symbol values.

Any suitable processor, display and input means may be used to process, display, store and accept information, including computer programs, in accordance with some or all of the teachings of the present invention, such as but not limited to a conventional personal computer processor, workstation or other programmable device or computer or electronic computing device, either general-purpose or specifically constructed, for processing; a display screen and/or printer and/or speaker for displaying; machine-readable memory such as optical disks, CDROMs, magnetic-optical discs or other discs; RAMs, ROMs, EPROMs, EEPROMs, magnetic or optical or other cards, for storing, and keyboard or mouse for accepting. The term "process" as used above is intended to include any type of computation or manipulation or transformation of data represented as physical, e.g. electronic, phenomena which may occur or reside e.g. within registers and/or memories of a computer.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices.

BRIEF DESCRIPTION OF THE DRAWINGS

Certain embodiments of the present invention are illustrated in the following drawings:

FIG. 16 is a diagram of a codeword generated by the encoder of FIG. 4, in accordance with certain embodiments of the present invention;

FIG. 17 is a diagram of a codeword generated by the encoder of FIG. 6, in accordance with certain embodiments of the present invention;

DETAILED DESCRIPTION OF CERTAIN EMBODIMENTS

Apparatus and methods for operating a flash device are now described, which are characterized by use of Lee distance based codes in the flash device so as to increase the number of errors that can be corrected for a given number of redundancy cells, compared with Hamming distance based codes.

The Lee distance between two sequences of symbols is the absolute sum of differences. If there are two symbols, S1 and S2, which take values between 0 and p−1 where p is a prime number, then the Lee distance between these two symbols is then given by $$D(S_1, S_2) = \begin{cases} |S_1 - S_2| & |S_1 - S_2| < (p-1)/2 \\ p - |S_1 - S_2| & |S_1 - S_2| \geq (p-1)/2 \end{cases}.$$

The distance between two sequences Si and Ri is then given by $$\sum_{i=0}^{n-1} D(S_i, R_i)$$

where n is the number of symbols in each of the two sequences.

Thus, using the above distance, the measure between two sequences is the number of level shifts assuming that per symbol there is a maximum of one error, i.e. either a single positive shift or a single negative shift; the Lee distance measure is suitable since the fact that multiple shifts per symbol are rare is now taken into account. Generally speaking, gain, compared with binary BCH, results from the fact that less bits are now used to store a full symbol.

In the described embodiments of the present invention, the use of the terms flash memory, flash memory device, flash memory apparatus, solid state disk, memory device and similar is non-limiting and interchangeable (also referred to in general as "storage apparatus"). In certain embodiments of the present invention, the elements associated with the storage apparatus as well as the sequence of operations carried out, are integral to the storage apparatus. In certain other embodiments of the present invention, at least some of the elements associated with the storage apparatus and at least some of the related operations are external to the flash, the solid state disk etc. For example, some of the operations performed by microcontroller 110 of FIG. 18A may be carried out by the central processing unit of the host 100, without limiting the scope of the present invention. For convenience only, the following description of certain embodiments of the present invention refers mainly to the term flash memory or solid state disk, however those versed in the art will readily appreciate that the embodiments that are described with reference to flash memory or solid state disk are likewise applicable mutatis mutandis to other storage apparatuses.

Although the applicability of the current invention is not limited to Flash memory devices, these are considered throughout for the sake of brevity.

Figure 18A:
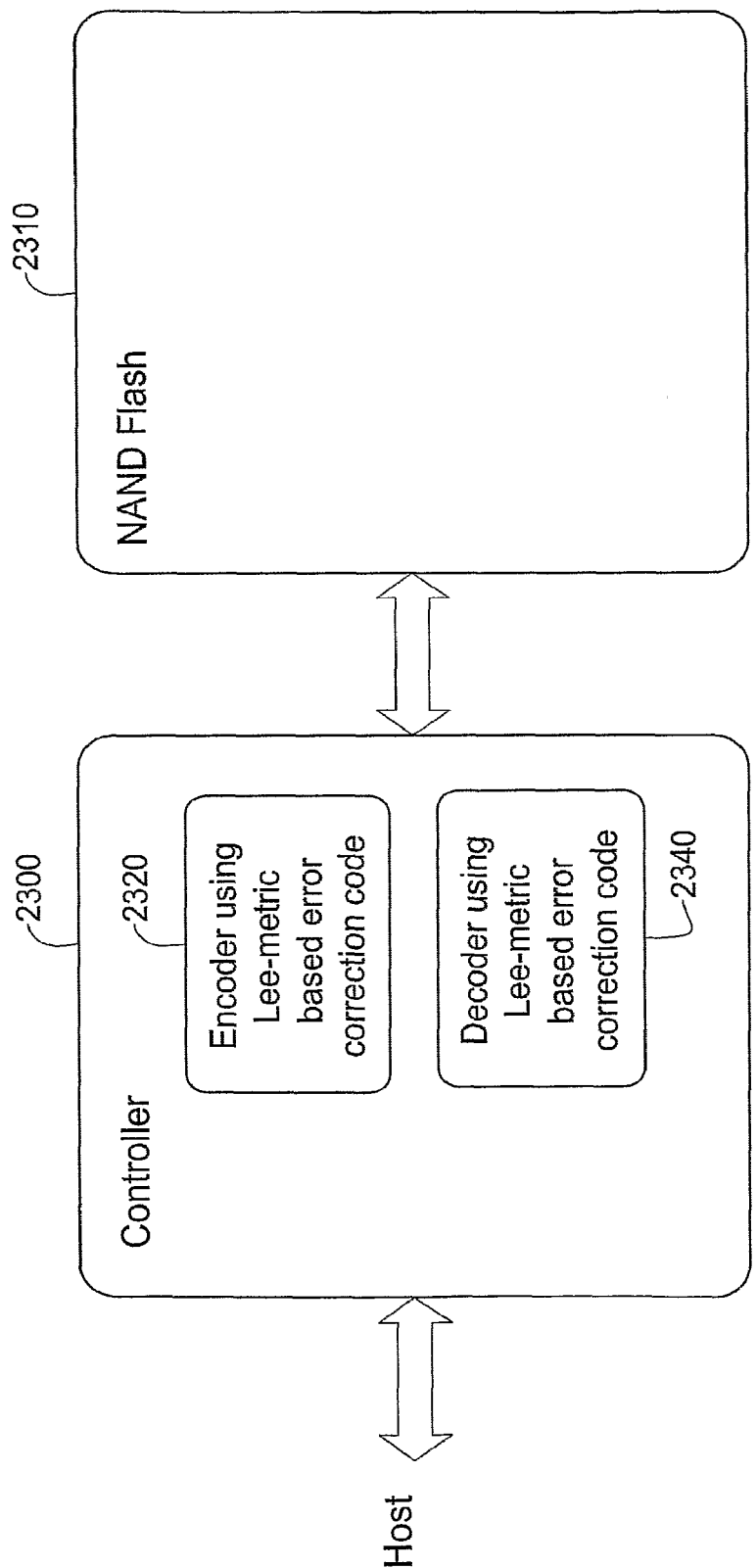
FIG. 18A is a simplified functional block diagram illustration of a NAND Flash device interacting with an external controller with Lee-metric based error correction encoding & decoding functionality in accordance with certain embodiments of the present invention.

One application of this invention, as shown in FIG. 18A, is in NAND Flash applications such as SD cards and USB drives. In these applications, the system comprises a controller 2400 and at least one NAND flash 2405 and perhaps many such as shown. The controller 2400 interfaces to a host through a specified protocol. For example, in the case of a USB drive the protocol is that defined by universal serial bus protocol. The controller 2400 then translates commands from the host. For example, read/write commands are translated into page read, page program and block erase commands on the Flash device 2405 through the NAND interface protocol. In order to combat errors which may occur in the multi-level NAND flash devices, code operative in accordance with certain embodiments of this invention may be employed, e.g. by adding an encoding operation to each program command and adding a decoding operation to each read command. The encoding/decoding operations shown and described herein may replace existing encode/decode operations using less efficient codes.

Figure 19:
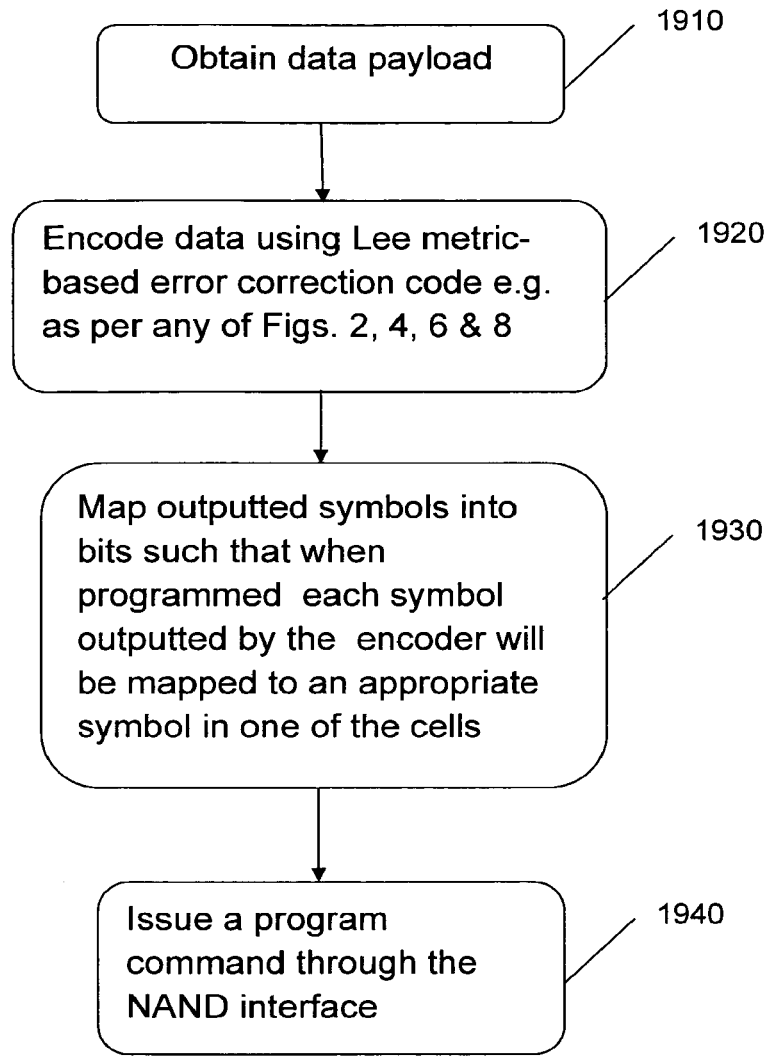
FIG. 19 is a simplified flowchart illustration of a method for effecting a NAND flash program command issued by the controller of FIG. 18A, in accordance with certain embodiments of the present invention.
Figure 20:
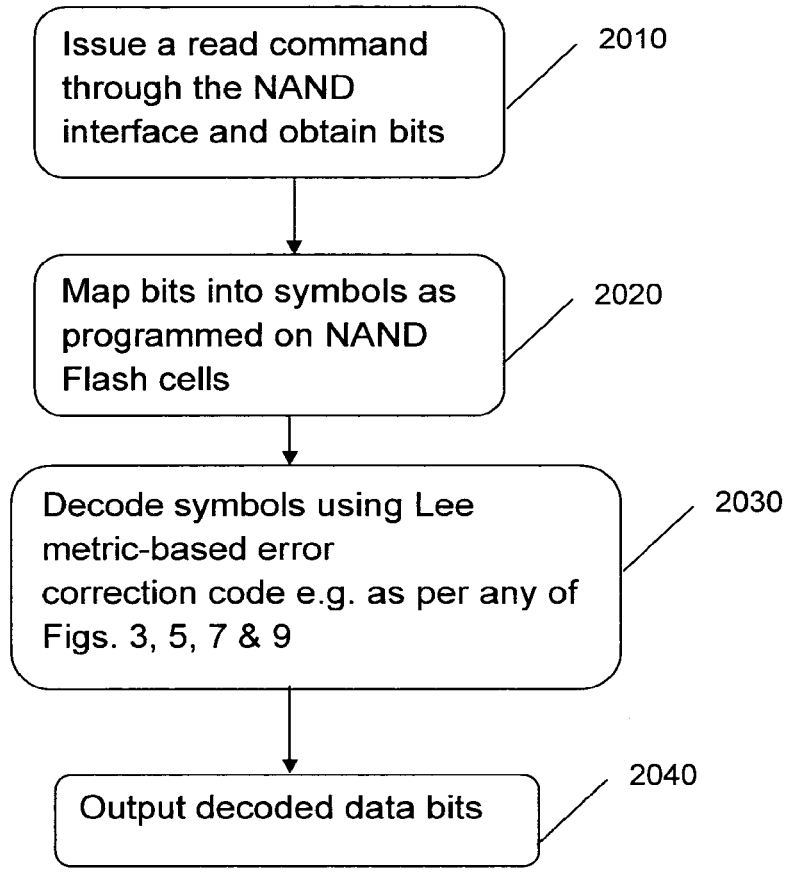
FIG. 20 is a simplified flowchart illustration of a method for effecting a NAND flash read command issued by the controller of FIG. 18A, in accordance with certain embodiments of the present invention.

The NAND devices 2405 are programmed page by page where each page may contain cells that store data and cells that store redundancy. Both sets of cells are used, such that the data and redundancy are spread over both. In the course of a NAND Flash interface program and read commands the page data is transferred as a sequence of bits and the bits are then mapped into cells. During a program or read command issued by the controller 2400, the output of encoder 2320 is mapped into bits such that when stored in the Flash device, the bits are mapped back into symbols in Flash cells as defined by the encoders' output. This process is shown in FIG. 19, for a programming procedure, and in FIG. 20, for a read command.

Taking a 4-level multi-level cell (MLC) device as an example, it is common to match each physical page (i.e. page in the Flash array 2420) into two logical pages such that each cell contains a bit from each of the logical pages, mapped using Gray coding. Here, the basic unit is two logical pages and each NAND flash read/program command is a sequence of two read/program commands of a logical page.

Figure 18B:
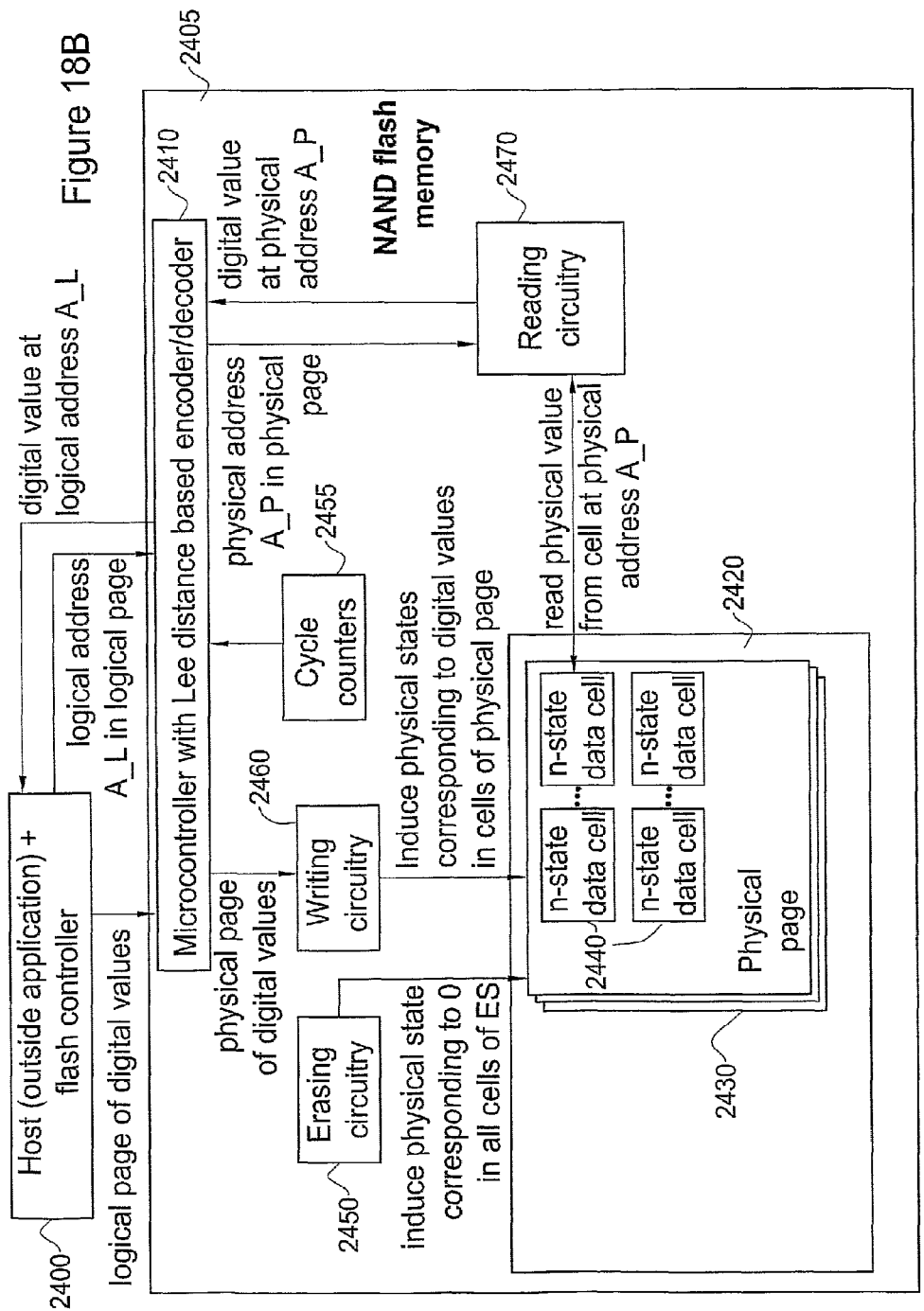
FIG. 18B is a simplified functional block diagram illustration of a flash memory system including an on-board microcontroller, with Lee-metric based error correction encoding & decoding functionality in accordance with certain embodiments of the present invention, wherein the encoding functionality may comprise any of the encoders of FIGS. 2, 4, 6 and 8 and the decoding functionality may comprise any of the decoders of FIGS. 3, 5, 7 and 9 respectively.

Alternatively, as shown in FIG. 18B, a flash memory device may be provided whose internal or on-board microcontroller has Lee metric-based error correction encoder/decoder functionality capable of effectively correcting more errors than a binary BCH code for a given length of redundancy. Four examples of encoding and decoding schemes in accordance with certain embodiments of the present invention, are now described, which employ four example codes respectively, termed the "syndrome separate" code, "syndrome separate, redundancy & data mixed" code, the "syndrome separate & shortened" code and the "syndrome separate & shortened, redundancy & data mixed" code respectively. Encoders and decoders employing these codes respectively, each constructed and operative in accordance with certain embodiments of the present invention are presented in FIGS. 2 and 3; 4 and 5; 6 and 7; 8 and 9 respectively.

The codes are used to encode information over a multi-level physical medium such as a Flash memory. Thus, the inputs and outputs of the Flash device are symbols containing L levels denoted by "0", "1", "2", through "L−1". The inputs to the encoder are always assumed to be a sequence of bits while the inputs to the decoder are assumed to be a sequence of Flash symbols. The flash symbols could be represented as a subset of a finite field. More precisely, these symbols may be viewed as a subset of a finite-filed GF(p) where p is a prime number.

The encoders receive k bits, where k is a predetermined constant, and produce n symbols, where n is a predetermined constant. n is such that $n*\log_2 L > k$ where $n*\log_2 L - k$ is, generally speaking, the number of spare bits allocated for the code for error correction purposes.

Figure 1:
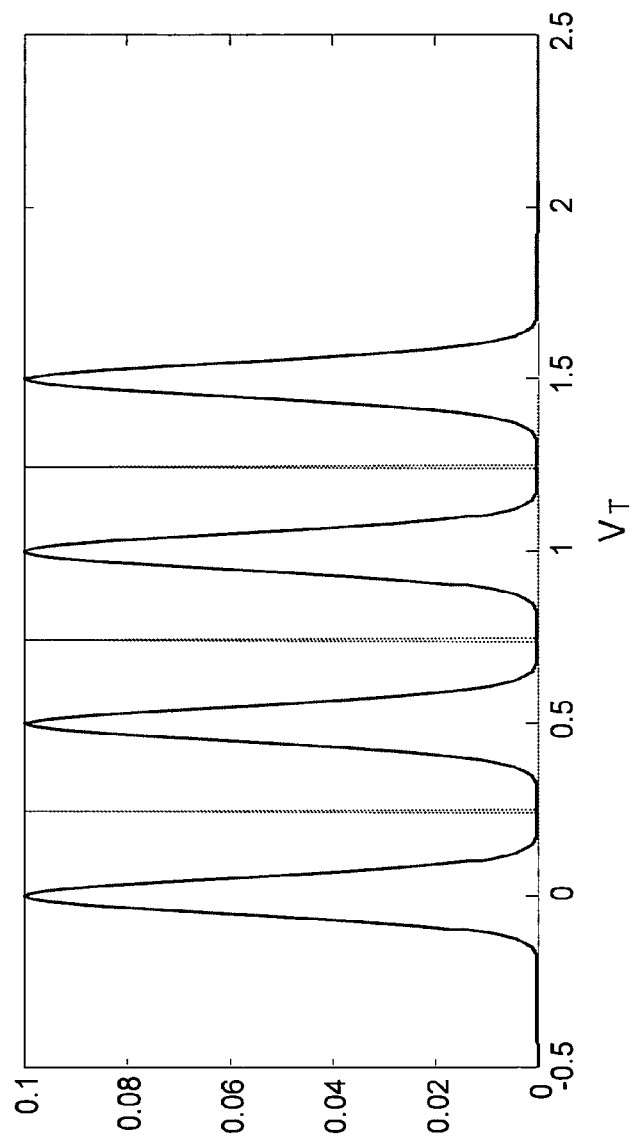
FIG. 1 is a prior art graph of physical level distributions in a two-bit per cell flash memory device.
Figure 2:
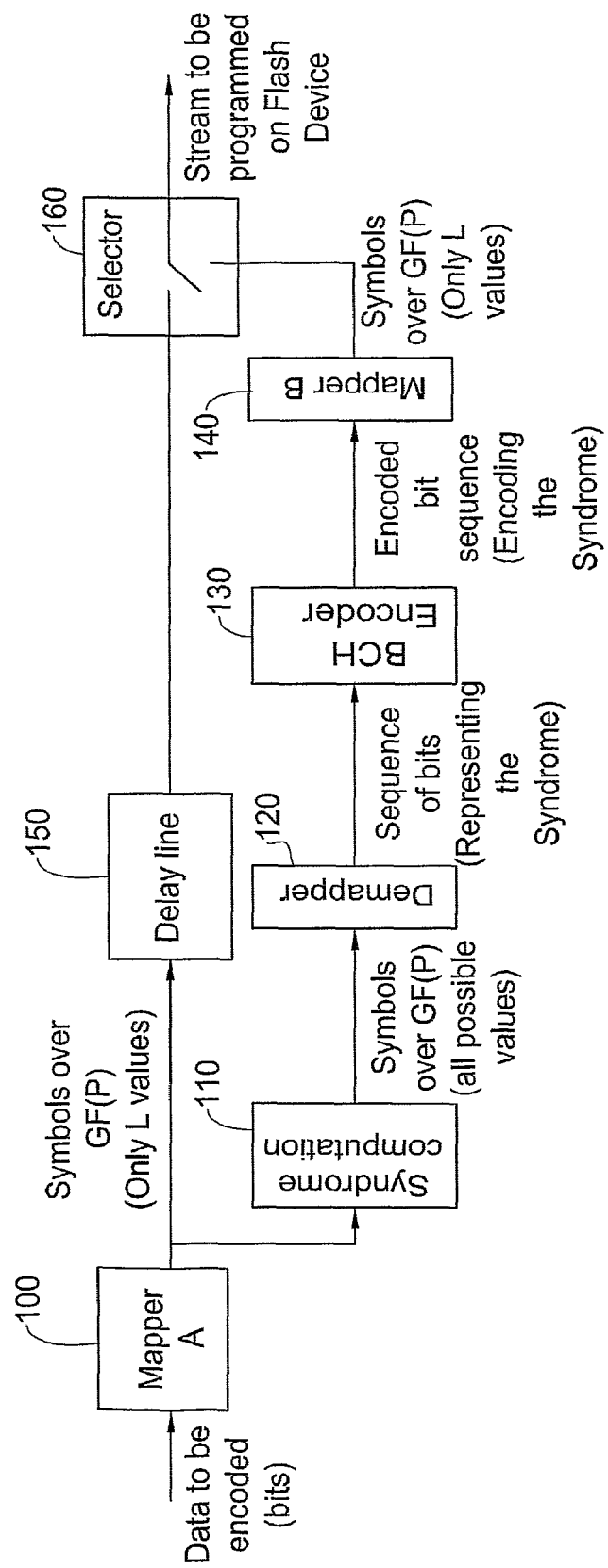
FIG. 2 is a simplified functional block diagram of a "syndrome separate" encoder constructed and operative in accordance with certain embodiments of the present invention.

The "syndrome separate" code is characterized by a separately encoded syndrome. The "syndrome separate" code is now described with reference to FIGS. 2 and 3, and using the following symbols:

k—number of data bits to be encoded
n—number of symbols in encoded word
L—number of levels
r—number of bits to be encapsulated by Mapper A (100 in FIG. 2)
t—number of symbols produced by Mapper A (100)
p—the smallest prime larger than t
$D_i$ (i=0 . . . t−1)—output symbols of Mapper A (100) comprising numbers in GF(p) with values between 0 and L−1.
w—number of symbols produced by the Syndrome Computation block (110) of FIG. 2.
$S_j$ (j=0 . . . w−1)—output symbols of the Syndrome computation block (110) comprising numbers in GF(p).
α—a non-zero element of GF(p) which is also a primitive element in GF(p).
k'—the number of bits mapped by the Demapper unit (120) following the mapping of the w symbols outputted by the Syndrome Computation block (110).
n'—number of bits at the output of the BCH encoder unit (130).
r'—number of symbols encapsulated at once by the Demapper unit (120).

Figures 10A, 10B, 11:
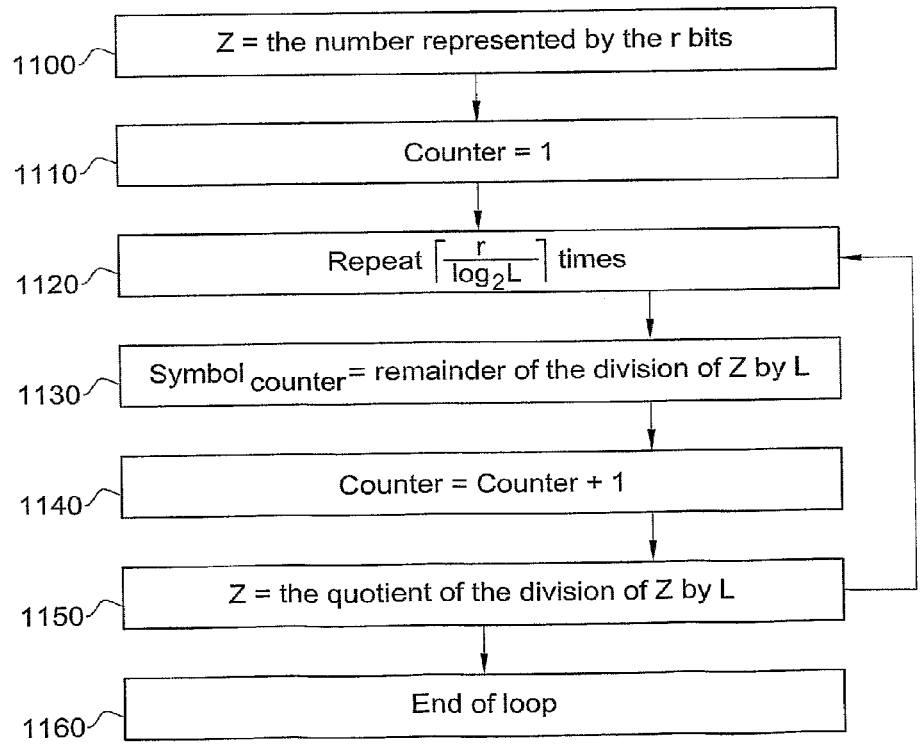
FIG. 10A is a table representing a first mapping scheme in which each subsequence is mapped into a number represented by the binary representation of that sequence.
FIG. 10B is a table representing a second mapping scheme in which each subsequence is mapped into a symbol using "Gray coding"
FIG. 11 is a simplified flowchart illustration of a method for encapsulating input data bits, in accordance with certain embodiments of the present invention.

FIG. 2 represents the "syndrome separate" encoder. The input to the encoder, a sequence of k bits, is mapped into t symbols by Mapper A (100). p is the smallest prime larger than or equal to t. If L is a power of 2, the data is divided into subsequences of $\log_2 L$ bits, each subsequence being mapped into a symbol between 0 to L−1, these symbols being numbers in the prime field GF(p). Mapping may be effected e.g. by mapping each subsequence into a number represented by the binary representation of that sequence as shown in the table of FIG. 10A. Another possibility is to use Gray coding as shown in the table of FIG. 10B. Gray coding is not crucial for Mapper A because the performance of the code is not degraded if a different mapping is used, due to the fact that the encoding scheme shown and described herein works on entire symbols and not on individual bits.

If L is not a power of 2 encapsulation may be used, typically dividing the input sequence into subsequences of r bits which are then translated into a sequence of $$\left\lceil \frac{r}{\log_2 L} \right\rceil$$

symbols over GF(p) where each symbol is one of 0, 1, ..., L−1. This may be done by representing the r bits as a number (in the standard number field) and following the procedure described in FIG. 11 to recover the symbols. In the method of FIG. 11, Z is, initially, the number represented by the r bits, and the following computations are repeated $$\left\lceil \frac{r}{\log_2 L} \right\rceil$$

times: Symbol$_{counter}$=remainder of the division of Z by L; and computation of Z as the quotient of the division of the previous Z by L. r is a predefined constant chosen to maximize the efficiency of encapsulation but yet sufficiently small to allow adequate implementation of the method in FIG. 11 either in hardware or software.

The output of Mapper A (100) then goes to a delay line block (150) and to a Syndrome computation block (110). The purpose of the delay line (150) is to delay the sequence of the t symbols produced by the Mapper A block (100) such that the first symbols produced by (140) follow immediately after the last symbol was outputted from delay line (150).

The Syndrome computation block (110) produces w elements in GF(p). As described above, the t symbols outputted from Mapper A block (100) are treated like numbers in the field GF(p). The Syndrome computation block (110) then performs the following computation:

$$S_j = \sum_{i=0}^{t-1} D_i \alpha^{ji}$$

where $D_i$ (i=0 ... t−1) are the output symbols of Mapper A (100), $S_j$ (j=0 ... w−1) are the output symbols of the Syndrome computation block (110) and a is a number between 1 and p−1 which is also a primitive element in GF(p). All multiplications and additions are carried out in the GF(p) field (i.e. modulo p). Finite fields, primitive elements, and other related aspects of the above computations are described in documents [2] and [3].

The output of the Syndrome computation unit (110) then flows to the Demapper unit (120). The Demapper maps the w GF(p) symbols into k' bits, again, typically by using encapsulation. That is, the w symbols are divided into subsets each including r' symbols, other than, possibly, one subset which has less than r' symbols. Each subset is then mapped into bits using the binary representation of the number (now in the standard field):

$$\sum_{i=0}^{r'-1} S_i p^i.$$

This number is mapped into a sequence of $\lceil r' \cdot \log_2 p \rceil$ bits.

The output of the Demapper (120) flows into a binary BCH encoder (130) which receives k' bits and produces n' bits which include, on top of the original k' bits, additional n'−k' redundancy bits which are used for error correction in the decoding process. The binary BCH encoder is a standard encoder as is known in the art such as any of these described in references [1], [2] and [3] and designed to function over $GF(2^{\lceil \log_2 n' \rceil})$.

The output of the binary BCH encoder (130) is then mapped into symbol Mapper B (140) which receives n' bits and maps them into n−t symbols. The mapping is performed similarly to that performed by Mapper A, typically using Gray coding. Again, if the number of levels is not a power of 2, encapsulation is effected as for Mapper A. If L is a power of 2 then the sequence of n' bits is simply divided into subsets of $\log_2 L$ bits. If the sequence does not exactly divide, the sequence is zero padded until it is divided by $\log_2 L$ without a quotient. The subsets of $\log_2 L$ bits are then mapped using Gray coding as shown e.g. in the table of FIG. 10B.

A Selector (160) enables the flow of either the mapped original data from the delay line or the mapped redundancy data from Mapper B (140). At first, typically the selector enables the delay line to flow out; once this has occurred, the output of Mapper B (140) flows out. The delay line is designed to delay the output of Mapper A (100) such that the output of Mapper B is synchronized to the end of the output of the delay line. The end result is a codeword as shown in FIG. 15.

Figure 15:
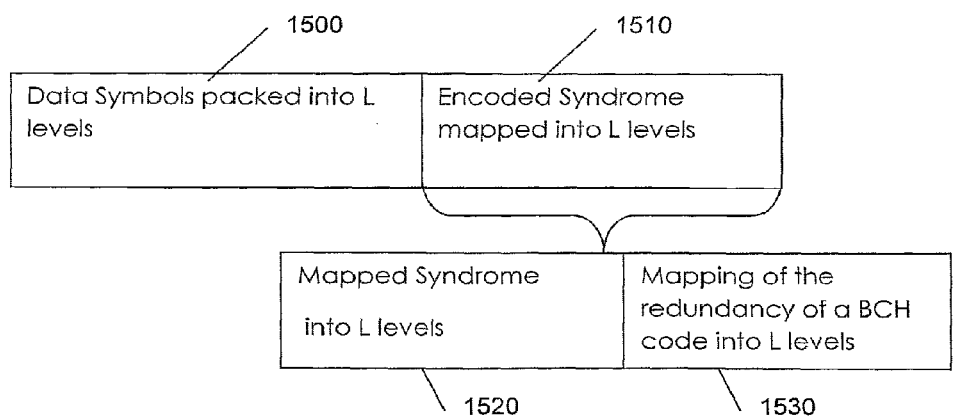
FIG. 15 is a diagram of a codeword generated by the encoder of FIG. 2, in accordance with certain embodiments of the present invention.

As shown, the codeword of FIG. 15 typically comprises a first portion (1500) which includes a mapping of the data sequence into L levels, and a second portion (1510) which is used as redundancy for the purpose of error correction of the information in the first portion 1500. Second portion 1510 is also mapped into L levels and also typically comprises two portions: a first portion (1520) including the mapping of the syndrome (computed from portion 1500) mapped into bits and then mapped to L levels; and a second portion (1530) including the mapping to L levels of the redundancy as computed by the BCH encoder of the portion (1520).

Figure 3:
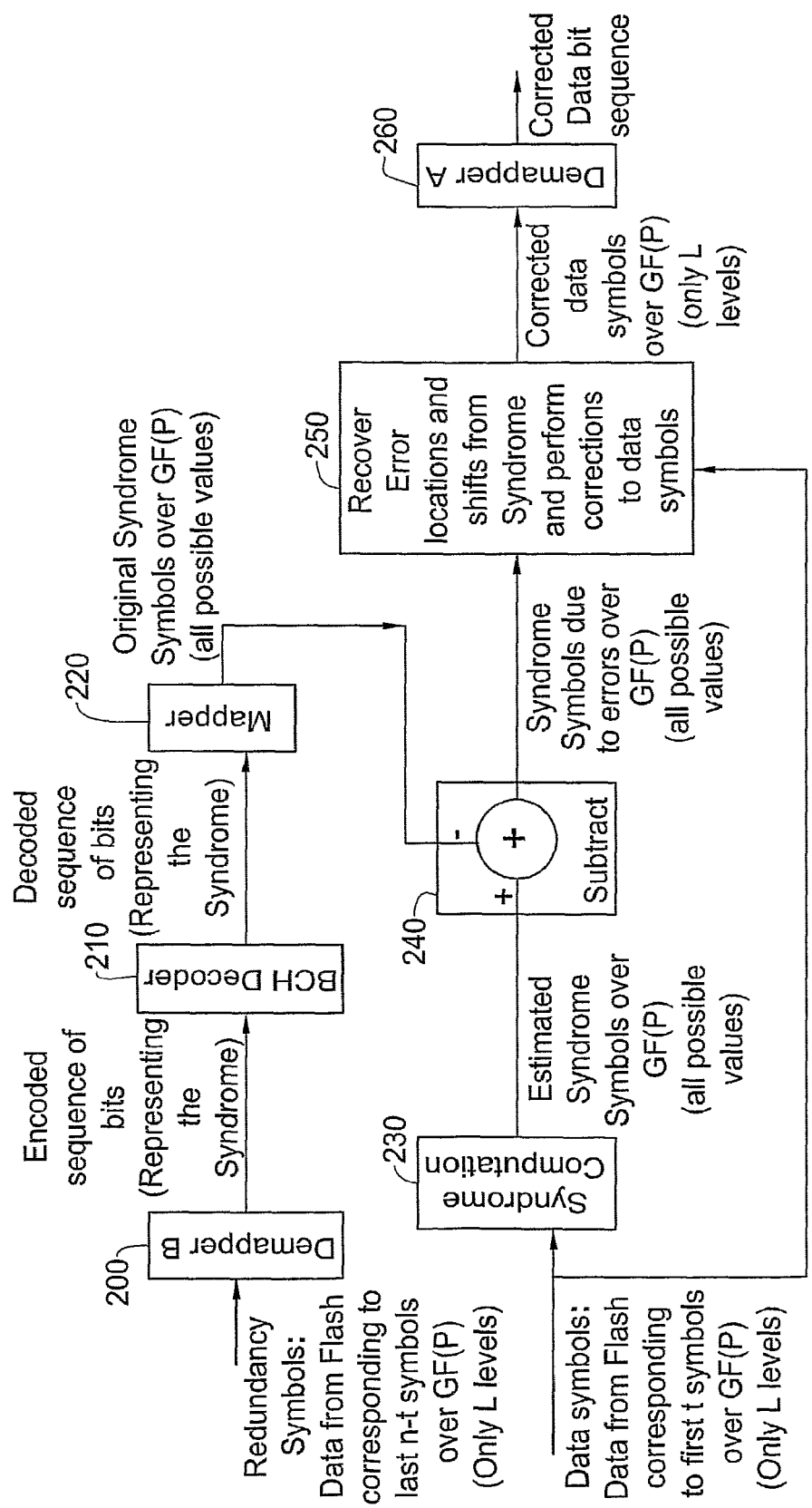
FIG. 3 is a simplified functional block diagram of a "syndrome separate" decoder constructed and operative in accordance with certain embodiments of the present invention.

FIG. 3 shows a schematic view of the "syndrome separate" decoder. The "syndrome separate" decoder of FIG. 3 typically receives n symbols from the Flash device and produces k correct bits. The n received symbols belong to one of L levels and may contain errors causing the wrong level to be read. The first t symbols are associated with actual data whereas the last n−t symbols are associated with redundancy.

The first t symbols and the last n−t symbols may be sent to the decoder of FIG. 3 simultaneously and analyzed simultaneously. If all n symbols are not sent simultaneously to the decoder, it is more efficient to send the last n−t symbols, which store the redundancy, first, followed by the first t symbols. The redundancy may then be decoded as the rest of the symbols are being sent to the decoder.

The first t symbols are sent to the Syndrome Computation unit which typically performs the same task as was performed by syndrome computation unit 110 in the "syndrome separate" encoder of FIG. 2. The last n−t symbols are sent to a Demapper B 200 which performs the converse of the operation performed by the Mapper B (140) in FIG. 2. The Demapper receives n−t symbols and produces n' bits.

Figure 12:
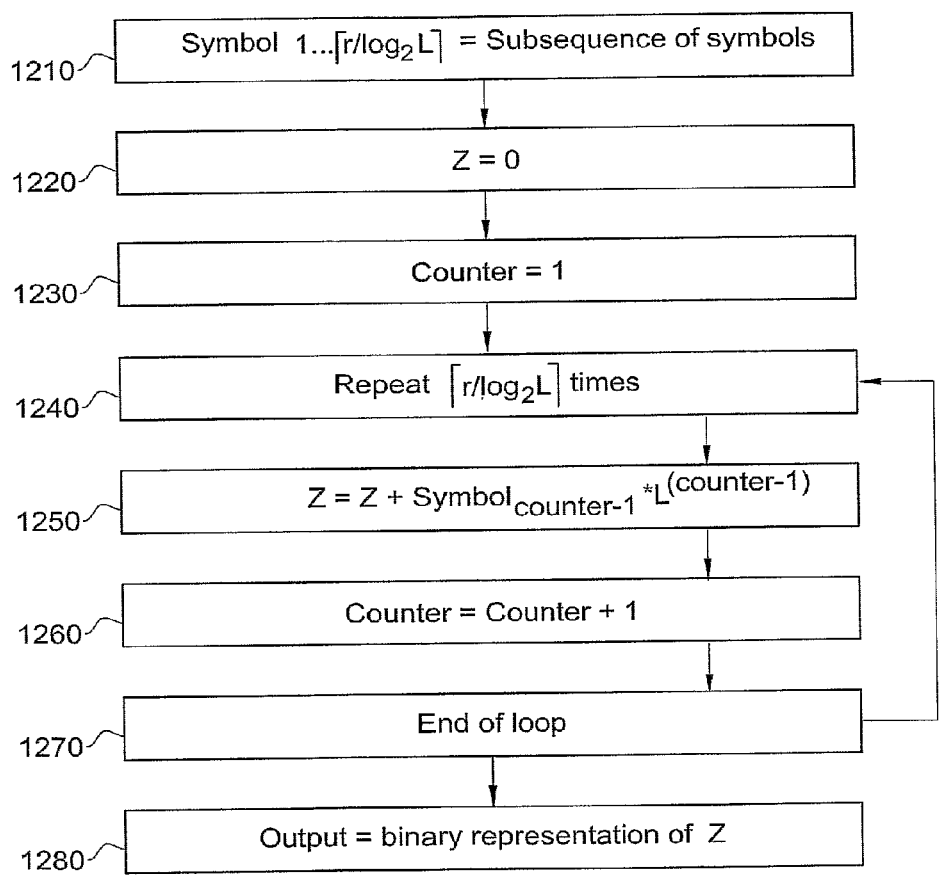
FIG. 12 is a simplified flowchart illustration of a method for de-encapsulation which may be performed by Demapper B in the decoder of FIG. 3, in accordance with certain embodiments of the present invention.

If the number of levels, L, is a power of 2, the Demapper 200 simply produces $\log_2 L$ bits for every symbol, the bits being produced by a process of Gray coding e.g. according to the table of FIG. 10B. If L is not a power of 2, de-encapsulation is performed to reverse the effect of encapsulation. That is, the n–t symbols are divided into sub-sequences of $\lceil r/\log_2 L \rceil$ symbols from which the Demapper B 200 produces r bits. FIG. 12 shows a procedure which may be employed to perform the De-encapsulation. In the method of FIG. 12, $\text{Symbol}_{0 \ldots \lceil r/\log_2 L \rceil}$ is a subsequence of symbols and Z is initially 0. $Z = Z + \text{Symbol}_{counter} * L^{(Counter-1)}$ is repeated $$\left\lceil \frac{r}{\log_2 L} \right\rceil$$

times and the output is the binary representation of the final value of Z.

The binary output of the Demapper 200 is a sequence of n' bits which are passed to the binary BCH decoder (210) which corrects any errors which might have occurred in the redundancy symbols. The BCH decoding may be effected as known in the art e.g. as described in references ([1], [2], [3]).

Figure 13:
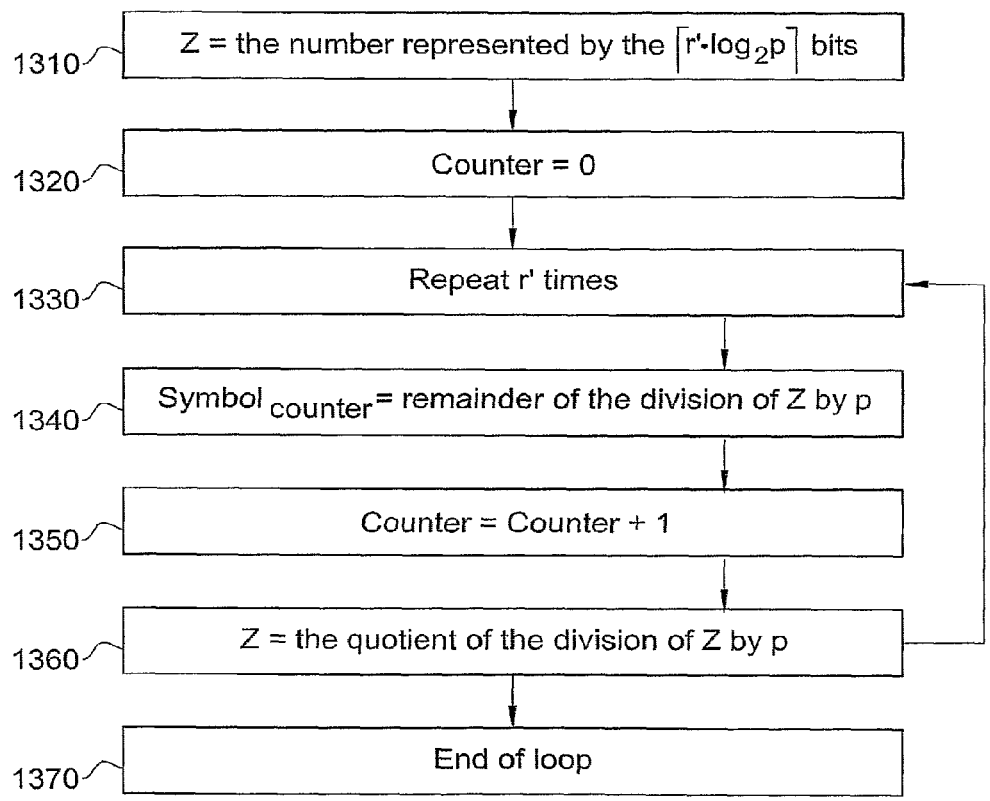
FIG. 13 is a simplified flowchart illustration of a method for de-encapsulation which may be performed by the mapper in the decoder of FIG. 3, in accordance with certain embodiments of the present invention.

The BCH decoder (210) outputs k' bits which were used to code the Syndrome during the encoding process performed by the encoder of FIG. 2. The k' bits are passed to a mapper unit (220) which produces w symbols over GF(p). This time the symbols may assume values from 0 to p–1. The mapper unit (220) performs the converse of the operation performed by the Demapper unit (120) in the encoder of FIG. 2, e.g. by De-encapsulation. The k' bits are divided into subsets of $\lceil r' \cdot \log_2 p \rceil$. The symbols may be derived by representing the subset as a number (in the normal field) and performing the method in FIG. 13. In the method of FIG. 13, Z, initially, is the number represented by the $\lceil r' \cdot \log_2 p \rceil$ bits and the following computations are repeated r' times: $\text{Symbol}_{counter} = $ remainder of the division of Z by p; and new Z=the quotient of the division of the current value of Z, by p.

The output of Mapper (220) is the accurate Syndrome whereas the output of the Syndrome Computation unit (230) is the estimated syndrome according to the received symbols from the device. The difference between them is the syndrome only due to the error. Thus, the output of the subtract block (240) is the difference (symbol by symbol) of the two syndromes and is the syndrome of the errors that occurred in the first t symbols. Using the output of the subtraction unit 240, the eligible word which is closest (by the Lee metric) to the word actually received, is recovered by best eligible word recovery block 250. Any suitable conventional method can be used to effect the recovery, such as that described in steps 2-5 on page 311 Section 10.4 ("Decoding alternant codes in the Lee metric"), in reference [2]. Once the correct symbols have been recovered, Demapper A (260) maps the t symbols back into k bits. The Demapper A undoes the operation of Mapper A (100) in the "syndrome separate" encoder of FIG. 2, similarly to Demapper B. However, it is not necessary to use Gray mapping.

Parameter determination according to certain embodiments of the present invention is now described. The length of the input sequence (in bits) and the length of the code word (in symbols) are given by conventional design preferences that are typically unaffected by the teachings of the invention shown and described herein, so k and n are assumed to be known. Therefore, values for the constant p and the number of symbols that contain data t are also immediately available. The encapsulation parameters r and r' are determined by hardware complexity restrictions; for example, r may not be limited to less than 128 bits. The remaining parameters may be determined by trading off the number of BCH redundancy bits n'–k' and the number of Syndrome symbols w, it being appreciated that n' bits may be stored in n–t symbols. The tradeoff is typically between the number of bits (n'–k') allocated to correct the "accurate" Syndrome and the number of symbols (w): allocated to correct the data referred to above, as stored in the word referred to above.

$P_{err}$ denotes the frame error rate and $P_{cross}$ denotes the probability that an individual level is erroneously read as either the following or preceding level. The probability of error may be approximated by assuming that errors only occur between nearby levels.

A decoding error may occur if either one of the following events occurs:
1. An error occurs in the decoding of "accurate" Syndrome (210). i.e., there were more than $\lfloor (n'-k')/\lceil \log_2 n' \rceil \rfloor$ errors in the (n–t) symbols allocated to store the redundancy.
2. An error occurs in the decoding of the data symbols using the Lee metric decoder (240). i.e., there were w or more errors in the first t symbols.

The probability of any of these events may be bounded from above by $$P_{err} \leq \sum_{i=\lfloor (n'-k')/\lceil \log_2 n' \rceil \rfloor + 1}^{n-t} \frac{(n-t)!}{i!(n-t-i)!}\left(\frac{2L-2}{L}p_{cross}\right)^i\left(1-\frac{2L-2}{L}P_{cross}\right)^{n-t-i} + \sum_{i=w}^{t} \frac{t!}{i!(t-i)!}\left(\frac{2L-2}{L}p_{cross}\right)^i\left(1-\frac{2L-2}{L}P_{cross}\right)^{t-i}$$

Thus, by enumerating over w, a value may be selected which reduces the above probability, typically to a minimum.

In "syndrome separate, redundancy & data mixed" code the redundancy symbols are no longer separated from the data symbols but rather mixed with them. This is done in such a manner that the error probability in the redundancy information is decreased. The downside is that p (the prime used for the Lee-metric code) increases with respect to n, which may decrease the error correction capability of the Lee-metric decoder. The number of levels, L, is assumed above to be a power of 2. However, where L is not a power of 2, encapsulation may be used, as described generally above. The following symbols are used in the description of the "syndrome separate, redundancy & data mixed" code:

k—number of data bits to be encoded
n—number of symbols in encoded word
L—number of levels
t—number of symbols produced by Mapper A (300).
p—the smallest prime larger than n
$D_i$ (i=0 . . . n–1)—Combined symbol output of Mapper A (300) and A' (310) comprising numbers in GF(p) with values between 0 and L–1.
w—number of symbols produced by the Syndrome Computation block (340)
$S_j$ (j=0 . . . w–1)—output symbols of the Syndrome computation block (340) comprising numbers in GF(p).
k'—the number of bits mapped by the Demapper unit (350) following the mapping of the w symbols outputted by the Syndrome Computation block (340).

n'—number of bits at the output of the BCH encoder unit (360).

$b_i$—bit i (=0 ... n'–1) of the output sequence of the BCH encoder unit (360).

$Y_i$—the symbols (i=0 ... n–1) at the output of the Mapper B (370) unit.

Figure 4:
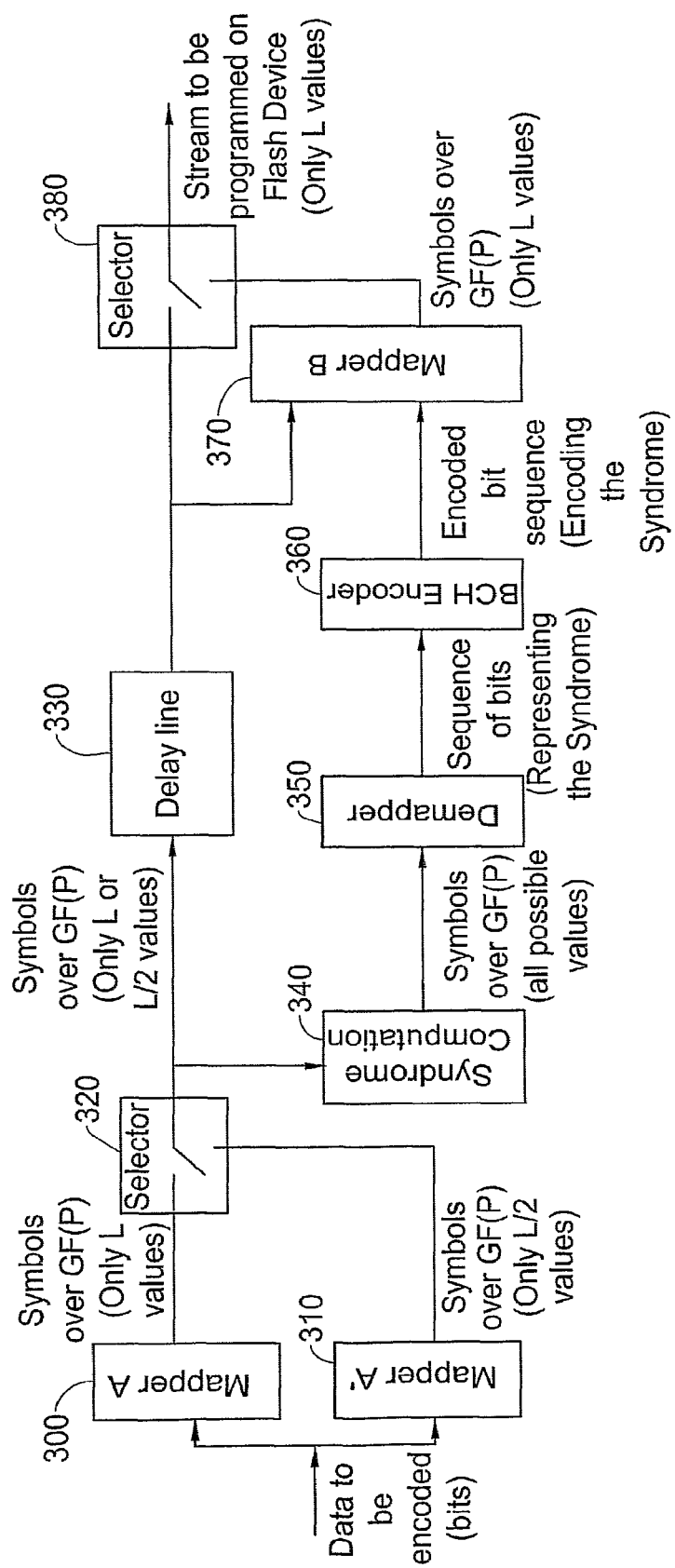
FIG. 4 is a simplified functional block diagram of a "syndrome separate, redundancy & data mixed" encoder constructed and operative in accordance with certain embodiments of the present invention.

FIG. 4 shows a schematic view of an encoder for the "syndrome separate, redundancy & data mixed" code. The input is a sequence of bits (k bits) which flows into Mappers A (300) and A' (310). The first $t \cdot \log_2 L$ bits are mapped by Mapper A into symbols over GF(p) with values between 0 and L–1. Mapper divides the $t \cdot \log_2 L$ bits into subsequences of $\log_2 L$ which are mapped into symbols using any type of mapping (for example the mappings in the tables in FIG. 10). It is appreciated that the choice of the mapping does not affect the performance of the code. The last $k-t \cdot \log_2 L$ bits of the input sequence are mapped by Mapper A' into symbols over GF(p) with values between 0 and L/2–1. This is done by dividing the remaining bits into subsequences of $\log_2 L-1$ bits and mapping the subsequences into symbols according to any mapping scheme.

The Selector (320) simply adjust the flow of the symbols such that the symbols generated by Mapper A' (310) follow the last symbols generated by Mapper A (300). Overall, there are n symbols (i.e. $n=t+\lceil (k-t \cdot \log_2 L)/(\log_2 L-1) \rceil$).

The symbols flow into the syndrome computation unit (340) which performs the same task as performed by the syndrome computation unit (110) in the "syndrome separate" encoder of FIG. 2. This unit produces w symbols over GF(p) (this time, the symbols take any value between 0 and p–1).

The w symbols then flow into the Demapper (350) which performs the same task as performed by the Demapper unit (120) in the "syndrome separate" encoder. The output of the Demapper (350) is k' bits which flow into the binary BCH encoder (360) which produces n' bits. Again, unit 360 is identical to unit 130 in the "syndrome separate" encoder of FIG. 2.

The output of the BCH encoder (360) then flows into Mapper B (370). The purpose of Mapper B is to combine the outputs of the Mapper A' (310) with the output of the BCH encoder. More precisely, Mapper A' (310) produces $\lceil (k-t \cdot \log_2 L)/(\log_2 L-1) \rceil$ symbols with values between 0 and L/2–1. The BCH encoder (360) produces n' bits. Typically, $n'=\lceil (k-t \cdot \log_2 L)/(\log_2 L-1) \rceil$. That is, t n-n'. The combined output is a symbol with values between 0 and L–1. This is done using the following formula:

$$Y_i = D_i + b_i \cdot L/2, \quad i = n-n' \ldots n-1,$$

where $Y_i$ are the symbols at the output of the Mapper B (370) unit, $D_i$ are the symbols at the output of the Selector unit (320) and $b_i$ are the bits (with values of 0 and 1) at the output of the BCH encoder (360).

The purpose of the Delay Line (330) is to delay the sequence of the symbols such that symbols $i=n-n' \ldots n-1$ may enter Mapper B (370) when the output of the BCH encoder is ready. The selector unit 380 then outputs the first t symbols from the delay line and the rest of the n'=n–t symbols from Mapper B.

The end result of this process is a codeword structured as shown in FIG. 16 which comprises 2 portions. The first portion (2100) includes the mapping of $t \cdot \log_2 L$ data bits into L-level symbols. The second portion (2110) includes both data and redundancy mapped into L-level symbols. This is done by letting the data determine the $\log_2 L-1$ LSB bits of the index of the L-level symbol. The syndrome (after mapping it into bits) and the redundancy of the BCH codes determine the most significant bit of the index of the L-level symbol.

Figure 5:
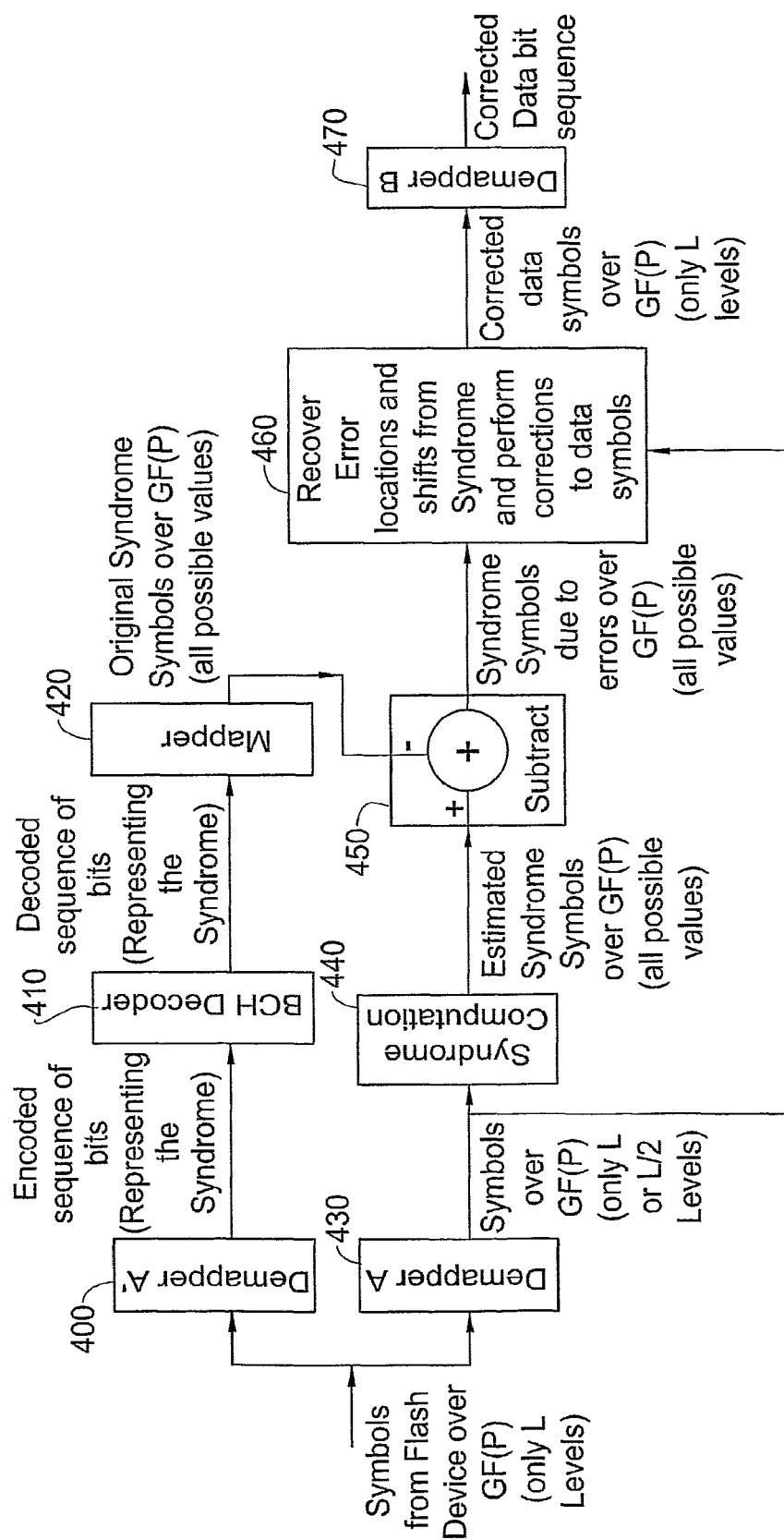
FIG. 5 is a simplified functional block diagram of a "syndrome separate, redundancy & data mixed" decoder constructed and operative in accordance with certain embodiments of the present invention.

FIG. 5 gives a schematic view of a decoder for the "syndrome separate, redundancy & data mixed" code. The n symbols of the code flow simultaneously into Demapper A' (400) and Demapper A (430). Demapper A (430) handles separately the first t symbols and the latter n' symbols. The first t symbols are passed 'as is' to the Syndrome computation unit (440) while the latter n' symbols are stripped from the Redundancy information produced by the BCH encoder (360) in the encoder. This is done as follows:

$$\hat{F}_i = \begin{cases} F_i & i = 0 \ldots t-1 \\ \mathrm{rem}(F_i, 2^{L-1}) & i = t \ldots n \end{cases}$$

where $\hat{F}_i$ is the output of Demapper A and $F_i$ is the input. Demapper A' (400) only handles the last n' symbols and recovers from them only the redundancy bits produced by the BCH encoder by computing $b_i = \lfloor Y_i/(L/2) \rfloor$ for $i=t \ldots n-1$.

The output of Demapper A' (400) is a sequence of n' bits which are decoded by the binary BCH decoder (410) which produces k' bits. These bits are then mapped back into w symbols over GF(p) by the Mapper (420) which performs the same task as the Mapper (220) in the "syndrome separate" decoder of FIG. 3.

In parallel, the output of Demapper A (430) flows into the Syndrome computation unit (440) which performs the same task as the Syndrome computation unit (340) in the encoder. The output of Mapper (420) are the "accurate" syndrome symbols while the output of the syndrome computation unit (440) is a result of errors symbols. The difference between these syndromes (symbol by symbol) is the syndrome due to the errors alone. This difference is computed by the Subtract unit (450).

Unit 460 receives the output of 450 and Demapper A, and recovers the accurate symbols. Any suitable conventional method can be used to effect the recovery, such as that described in steps 2-5 on page 311 Section 10.4 ("Decoding alternant codes in the Lee metric"), in reference [2]. The output of 460 flows into the Demapper B (470) which performs the reverse operation of Mapper A (300) for symbols $0 \ldots t-1$ and Mapper A' (310) for symbols $t \ldots n-1$. The output is the reconstructed input stream.

Parameter Determination in accordance with certain embodiments of the present invention is now described. There is a degree of freedom lying, again, in the tradeoff between w which determines the k' and the ability to correct the data symbols and n'–k' which is the redundancy allotted for the BCH code and determines the ability to correct errors in the "accurate" syndrome. A decoding error may occur if either one of the following events occurs:

1. An error occurs in the decoding of "accurate" Syndrome (410). i.e., there were more than $\lfloor n'-k')/\lceil \log_2 n' \rceil \rfloor$ errors in the (n–t) symbols allocated to store the redundancy. The probability of bit error is $P_{cross}/(L/2)$.

2. An error occurs in the decoding of the data symbols using the Lee metric decoder (460) indicating that there were w or more errors in one of the n symbols.

The probability of any of these events may be upper-bounded by $$P_{err} \leq \sum_{i=\lfloor (n'-k')/\lceil \log_2 n' \rceil \rfloor + 1}^{n'} \frac{n'!}{i!(n'-i)!} \left(\frac{2}{L} P_{cross}\right)^i \left(1 - \frac{2}{L} P_{cross}\right)^{n'-i} +$$

$$\sum_{i=w}^{n} \frac{n!}{i!(n-i)!} \left(\frac{2L-2}{L} P_{cross}\right)^i \left(1 - \frac{2L-2}{L} P_{cross}\right)^{n-i}$$

Thus, by enumerating over w, a value may be selected which brings the above probability to a minimum.

The improvement in the above expression here compared with that obtained for the "syndrome separate" code is in the first summand which now includes a small probability: $P_{cross}(L/2)$. This probability may be compared with the probability appearing for the "syndrome separate" code after normalizing with the number of bits per symbol; the comparison being $$2P_{cross}/L \text{ vis a vis } 2P_{cross}/L \cdot \frac{L-1}{\log_2 L}.$$

The "syndrome separate & shortened" code, characterized by a separately encoded shortened Syndrome, is now described. The "syndrome separate & shortened" code embodiment improves the "syndrome separate" code embodiment at the expense of adding $w^2$ multiplications over GF(p). The following symbols are used to describe the "syndrome separate & shortened" code:

k—number of data bits to be encoded
n—number of symbols in encoded word
L—number of levels
r—number of bits to be encapsulated by Mapper A (500)
t—number of symbols produced by Mapper A (500)
p—the smallest prime larger than t+w
$D_i$ (i=0 ... t−1)—output symbols of Mapper A (500) comprising numbers in GF(p) with values between 0 and L−1.
w—number of symbols produced by the Syndrome Computation block (510)
$S_j$ (j=0 ... w−1)—output symbols of the Syndrome computation block (510) comprising numbers in GF(p).
$Z_j$ (j=0 ... w−1)—output symbols of block 520 comprising numbers in GF(p).
$V_j$ (j=0 ... w−1) and $T_j$ (j=0 ... w−1)—output symbols of block 530 comprising numbers in GF(p).
α—a non-zero element of GF(p) (i.e. a number between 1 and p−1).
k′—the number of bits mapped by the Demapper unit (540) following the mapping of the w symbols outputted from the Roundup unit (530).
n′—number of bits at the output of the BCH encoder unit (550).
r′—number of symbols encapsulated in unison (in parallel) by the Demapper unit (540).

Figure 6:
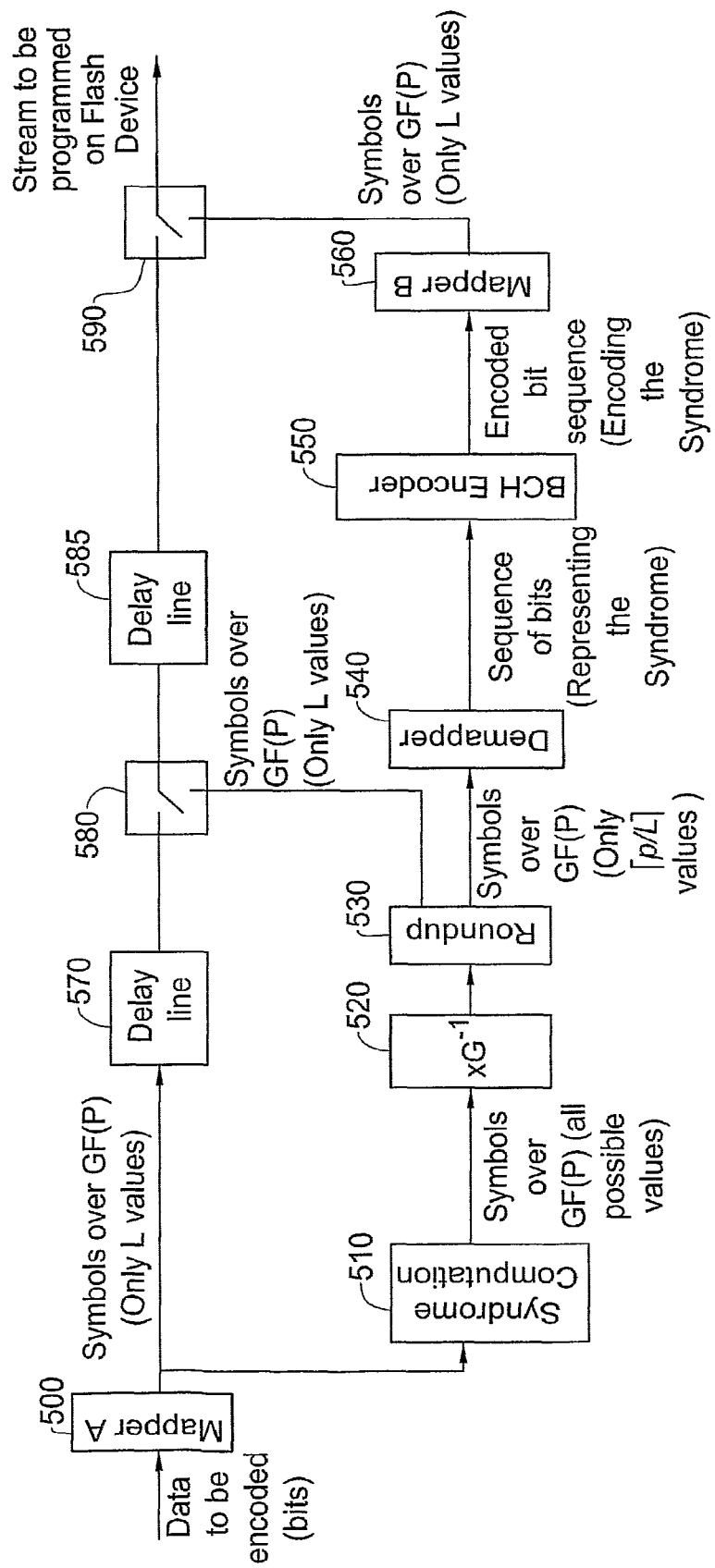
FIG. 6 is a simplified functional block diagram of a "syndrome separate & shortened" encoder constructed and operative in accordance with certain embodiments of the present invention.

FIG. 6 illustrates an encoder of the "syndrome separate & shortened" code which is similar to the "syndrome separate" encoder of FIG. 2 but includes 2 additional units: $xG^{-1}$ unit 520 and roundup unit 530. The operations of all other blocks substantially resemble the operations of their counterparts in FIG. 2, respectively. For example, as in the "syndrome separate" code embodiment, data in the form of a bit sequence flows into Mapper A (500) and then to the syndrome computation unit (510). Both units, 500 and 510, operate substantially as do their counterparts in the "syndrome separate" code encoder of FIG. 2, however the w-symbol output of the Syndrome computation unit (510) flows into a matrix multiplier $xG^{-1}$ (520) which multiplies the syndrome (as computed before) by the following matrix $G^{-1}$:

$$G^{-1} = \begin{pmatrix} \alpha^{t \cdot 0} & \alpha^{(t+1) \cdot 0} & \alpha^{(t+2) \cdot 0} & \cdots & \alpha^{(t+w-1) \cdot 0} \\ \alpha^{t \cdot 1} & \alpha^{(t+1) \cdot 1} & \alpha^{(t+2) \cdot 1} & & \\ \alpha^{t \cdot 2} & \alpha^{(t+1) \cdot 2} & \alpha^{(t+2) \cdot 2} & & \\ \vdots & & & \ddots & \\ \alpha^{t \cdot (w-1)} & & & & \alpha^{(t+w-1) \cdot (w-1)} \end{pmatrix}^{-1},$$

where α is the primitive element in GF(p) used in the computation of the syndrome. The multiplication operation is defined as follows:

$$\begin{pmatrix} Z_0 \\ Z_1 \\ \vdots \\ Z_{w-1} \end{pmatrix} = G^{-1} \begin{pmatrix} S_0 \\ S_1 \\ \vdots \\ S_{w-1} \end{pmatrix},$$

where $Z_i$ are the outputs of the matrix multiplication unit.

The output of the matrix multiplier flows into the Roundup unit 530 which adds a number $T_i$ between 0 and L−1 to each of the elements $Z_i$ such that $V_i = Z_i + T_i$ modulo p is divisible by L. The symbols $T_i$, which take only values between 0 and L−1, are outputted to the Selector unit (580) which appends these symbols to the end of the t symbols holding the data. The symbols $V_i$ flow to the Demapper unit (540). $V_i$ typically only have $\lceil p/L \rceil$ possible values, all divisible by L.

The Demapper unit (540) operates similarly to the Demapper (120) of the "syndrome separate" code encoder of FIG. 2, however before performing the encapsulation, the symbols are divided by L and in the encapsulation process, the parameter p is exchanged with $\lceil p/L \rceil$. This yields a more compact presentation of the syndrome and diminishes the BCH code's requirements, thus allowing a tradeoff between w and n′−k′ in the computation of the frame error rate to weigh in favor of w. The operations of the other units in FIG. 6 are similar to those of their counterparts in the "syndrome separate" encoder of FIG. 2. The end result is a codeword as shown in FIG. 17.

The codeword of FIG. 17 may include three portions. The first portion (2200) is simply a mapping of the data sequence into L levels. The second portion (2210) includes W L-level symbols which define a portion of the syndrome characterized in that the overall syndrome of the data symbols along with these W symbols has a significantly smaller set of possibilities. The third portion (2220) includes some of the encoded syndrome (only the portion thereof which was to be defined) and is used as redundancy for purpose of error correction of the information in the first two portions 2200 and 2210. The third portion 2220 is also mapped into L levels and comprises:

a first portion (2230) including the mapping of the total syndrome (computed from portion 2200 and 2210) mapped into bits and then mapped to L levels; and a second portion (2240) including the mapping to L levels of the redundancy as computed by the BCH encoder of the portion (2230).

Figure 7:
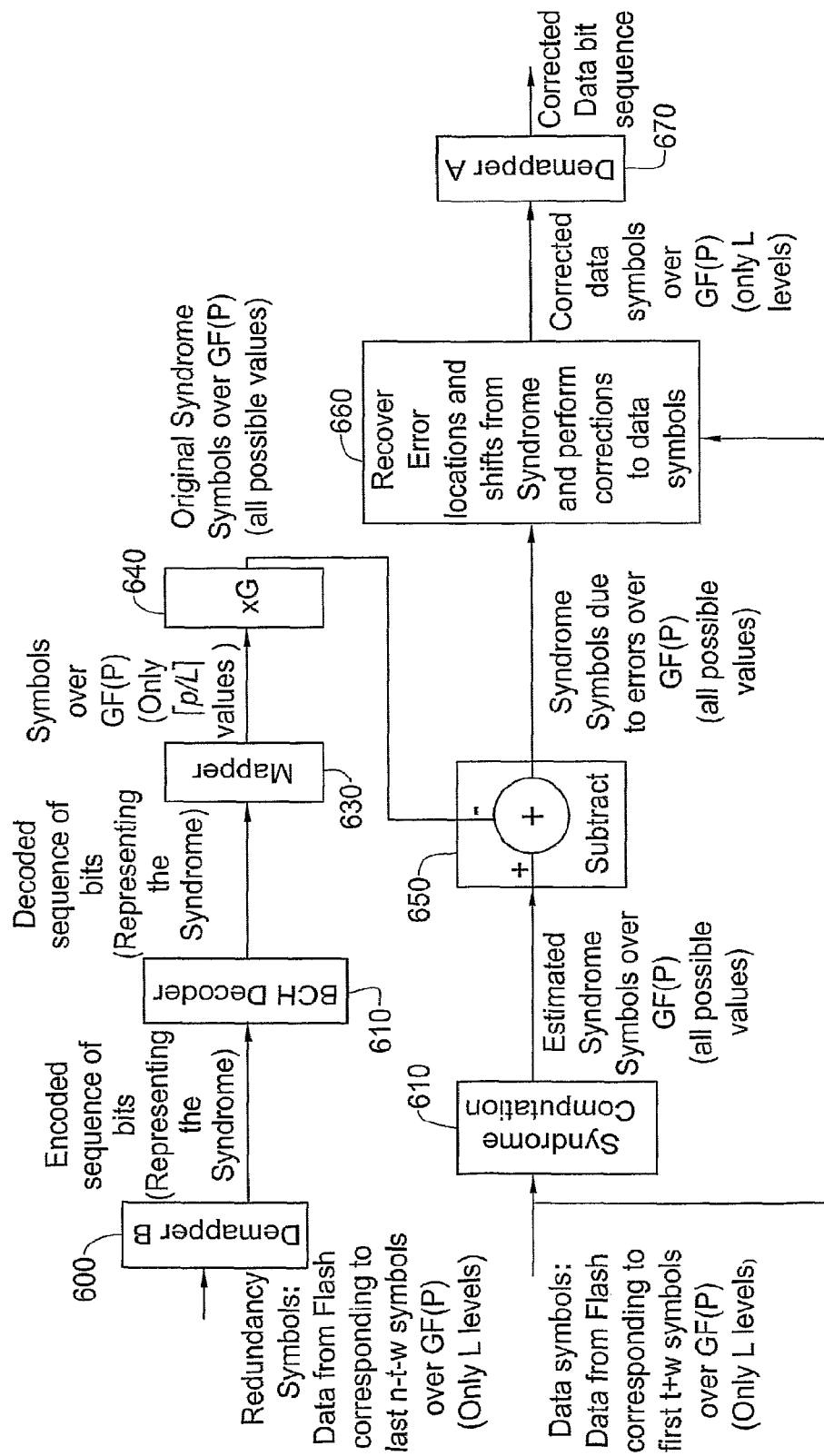
FIG. 7 is a simplified functional block diagram of a "syndrome separate & shortened" decoder constructed and operative in accordance with certain embodiments of the present invention.

FIG. 7 illustrates a "syndrome separate & shortened" decoder which is similar to the "syndrome separate" decoder of FIG. 3, however, a matrix multiplier unit xG (640) is provided which multiplies the W-symbol output of the Mapper unit (630) by the following matrix G:

$$G = \begin{pmatrix} \alpha^{t \cdot 0} & \alpha^{(t+1) \cdot 0} & \alpha^{(t+2) \cdot 0} & \cdots & \alpha^{(t+w-1) \cdot 0} \\ \alpha^{t \cdot 1} & \alpha^{(t+1) \cdot 1} & \alpha^{(t+2) \cdot 1} & & \\ \alpha^{t \cdot 2} & \alpha^{(t+1) \cdot 2} & \alpha^{(t+2) \cdot 2} & & \\ \vdots & & & \ddots & \\ \alpha^{t \cdot (w-1)} & & & & \alpha^{(t+w-1)(w-1)} \end{pmatrix}.$$

The Mapper unit (630) is similar to Mapper unit (220) in the "syndrome separate" decoder of FIG. 2, however, the parameter p is replaced with $\lceil p/L \rceil$ and the outputs are multiplied by L. Also, the syndrome computation unit (610) operates over t+w elements whereas its counterpart in the "syndrome separate" decoder of FIG. 2 operates over t elements. The remaining units in the "syndrome separate & shortened" decoder of FIG. 7 can be generally identical to their counterparts in the "syndrome separate" code decoder of FIG. 2.

Parameter Determination for the "syndrome separate & shortened" code embodiment of FIGS. 6 and 7 in accordance with certain embodiments of the present invention is now described. Computations for the "syndrome separate & shortened" code embodiment differ from those performed for the "syndrome separate" code to accommodate for the fact that a portion of the redundancy is passed to the Lee decoder and that k' and n' are now smaller. A decoding error may occur if either one of the following occurs:

1. An error occurs in the decoding of "accurate" Syndrome (610), e.g. there are more than $\lfloor (n'-k')/\lceil \log_2 n' \rceil \rfloor$ errors in the (n−t−w) symbols allocated to store the redundancy.
2. An error occurs in the decoding of the data symbols using the Lee metric decoder (660), e.g. there are w or more errors in the first t+w symbols.

The probability of either of these events may be bounded from above by $$P_{err} \leq \sum_{i=\lfloor (n'-k')/\lceil \log_2 n' \rceil \rfloor + 1}^{n-t-w} \frac{(n-t-w)!}{i!(n-t-w-i)!} \left(\frac{2L-2}{L}P_{cross}\right)^i \left(1 - \frac{2L-2}{L}P_{cross}\right)^{n-t-i} + \sum_{i=w}^{t+w} \frac{(t+w)!}{i!(t+w-i)!} \left(\frac{2L-2}{L}P_{cross}\right)^i \left(1 - \frac{2L-2}{L}P_{cross}\right)^{t+w-i}$$

Thus, by enumerating over w, a value may be selected which reduces the above probability, typically to a minimum.

The "syndrome separate & shortened, redundancy & data mixed" code, characterized by mixed data and an encoded shortened Syndrome, is now described. This code improves the "syndrome separate, redundancy & data mixed" code at the cost of adding $w^2$ multiplications over GF(p). The following symbols are used in the following description of the syndrome separate & shortened, redundancy & data mixed" code:

k—number of data bits to be encoded n—number of symbols in encoded word

L—number of levels t—number of symbols produced by Mapper A (700).

p—the smallest prime larger than n $D_i$ (i=0 . . . n−1)—Combined symbol output of Mapper A (700) and A' (710) Comprising numbers in GF(p) with values between 0 and L−1.

w—number of symbols produced by the Syndrome Computation block (740)

$S_j$ (j=0 . . . w−1)—output symbols of the Syndrome computation block (740) comprising numbers in GF(p).

$Z_j$ (j=0 . . . w−1)—output symbols of block 750 comprising numbers in GF(p).

$V_j$ (j=0 . . . w−1) and $T_j$ (j=0 . . . w−1)—output symbols of block 760 comprising numbers in GF(p).

k'—the number of bits mapped by the Demapper unit (780) following the mapping of the w symbols outputted by the Syndrome Computation block (740).

n'—number of bits at the output of the BCH encoder unit (790).

$b_i$—bit i (=0 . . . n'−1) of the output sequence of the BCH encoder unit (790).

$Y_i$—the symbols (i=0 . . . n−1) at the output of the Mapper B (800) unit

Figure 8:
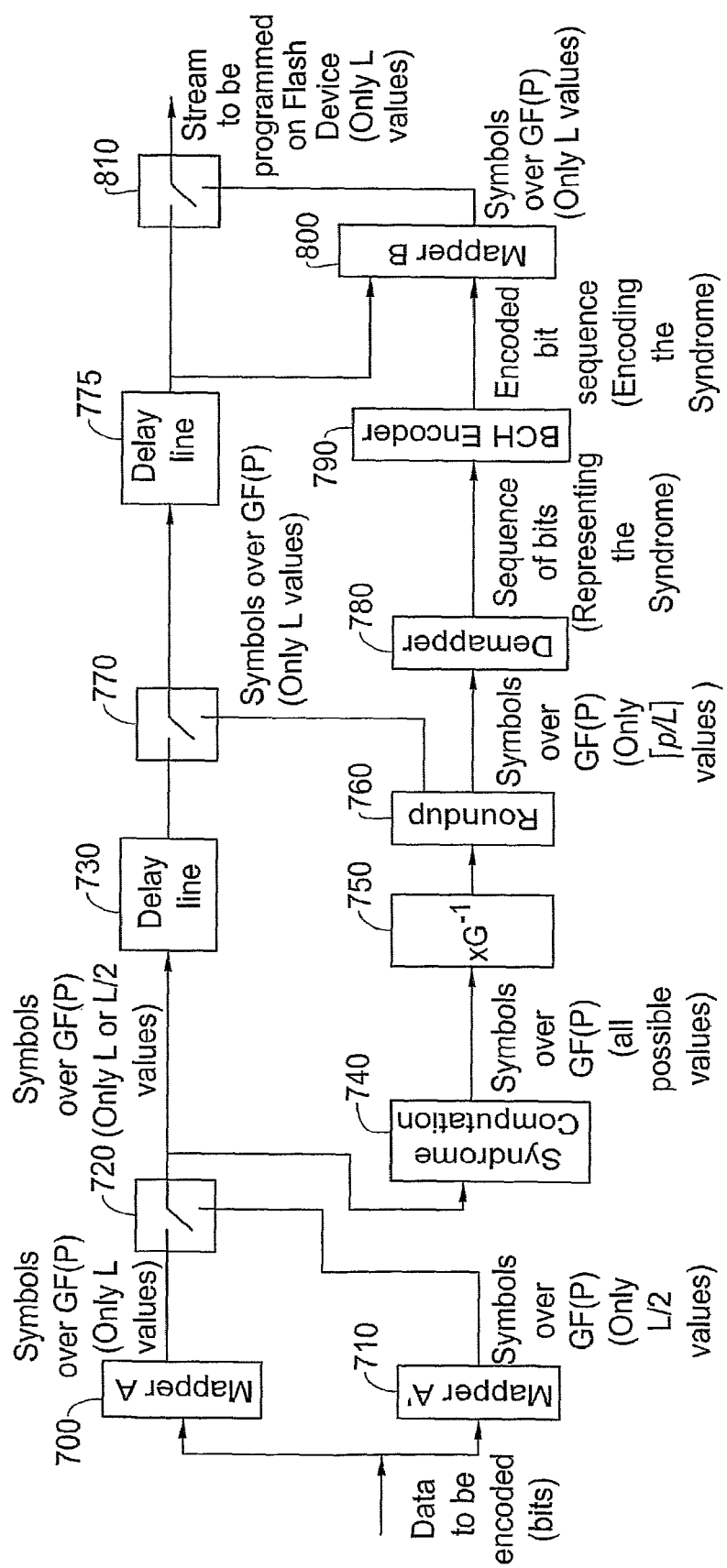
FIG. 8 is a simplified functional block diagram of a "syndrome separate & shortened, redundancy & data mixed" encoder constructed and operative in accordance with certain embodiments of the present invention.
Figure 14:
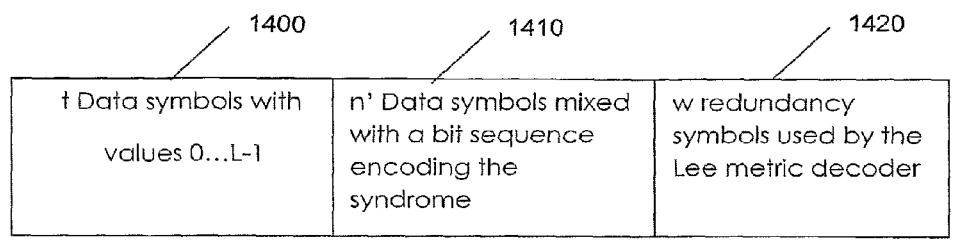
FIG. 14 is a diagram of a codeword generated by the encoder of FIG. 8, in accordance with certain embodiments of the present invention.

FIG. 8 illustrates a "syndrome separate & shortened, redundancy & data mixed" encoder. A difference between this encoder and the encoder of the "syndrome separate, redundancy & data mixed" code is that w additional symbols with values between 0 and L−1 are appended at the encoder of codeword 2, allowing the sequence of bits ($b_i$, i=0 . . . n'−1) used to encode the Syndrome to be shortened at the expense of adding w elements to the Lee decoding procedure. This guarantees a new tradeoff between w and the size of the redundancy of the BCH code e.g. (n'−k' bits). The composition of the codeword is shown in FIG. 14. The mid-section 1410 comprises both data bits and encoded syndrome bits (what is left of it following the use of the additional w symbols appended to the end of the codeword) as shown in FIG. 16 in portions 2120 and 2130.

Mapper A (700), Mapper B (710), Selector (720) and the syndrome Computation unit (740) may be generally identical to their counterparts in the "syndrome separate, redundancy & data mixed" encoder of FIG. 4 namely units 300, 310, 320 and 340 respectively. It is appreciated that in this embodiment, t=n−n'−w.

Downstream of the syndrome computation unit (740) are a matrix multiplier $xG^{-1}$ (750) and a roundup unit (760) which may be generally similar to their counterparts in the "syndrome separate & shortened" encoder of FIG. 6 namely units 520 and 530 respectively. The matrix multiplier $xG^{-1}$ (750) typically computes the following:

$$\begin{pmatrix} Z_0 \\ Z_1 \\ \vdots \\ Z_{w-1} \end{pmatrix} = \begin{pmatrix} \alpha^{(t+n')\cdot 0} & \alpha^{(t+n'+1)\cdot 0} & \alpha^{(t+n'+2)\cdot 0} & \cdots & \alpha^{(t+n'+w-1)\cdot 0} \\ \alpha^{(t+n')\cdot 1} & \alpha^{(t+n'+1)\cdot 1} & \alpha^{(t+n'+2)\cdot 1} & & \\ \alpha^{(t+n')\cdot 2} & \alpha^{(t+n'+1)\cdot 2} & \alpha^{(t+n'+2)\cdot 2} & & \\ \vdots & & & \ddots & \\ \alpha^{(t+n')\cdot (w-1)} & & & & \alpha^{(t+n'+w-1)\cdot (w-1)} \end{pmatrix}^{-1} \begin{pmatrix} S_0 \\ S_1 \\ \vdots \\ S_{w-1} \end{pmatrix}$$

where $Z_i$ are the outputs of the matrix multiplication unit.

The Demapper unit (780) may be similar to Demapper (350) of the "syndrome separate, redundancy & data mixed" encoder of FIG. 4, however typically, before demapper 780 performs encapsulation, the symbols are divided by L and in the encapsulation process, the parameter p is exchanged with $\lceil p/L \rceil$, all in contrast to demapper 350, to provide a more compact presentation of the syndrome and diminish the requirements from the BCH, thereby allowing the tradeoff between w and n'-k' in the computation of the frame error rate to weigh in favor of w. The operation of the other units may be similar to that of their counterparts in the "syndrome separate, redundancy & data mixed" encoder of FIG. 4 except that the Mapper 800, unlike its counterpart, mapper 370 in the "syndrome separate, redundancy & data mixed" code embodiment, effects mixing of the bits $b_1$ from the BCH encoder 790 and the channel symbols for symbols t . . . t+n'−1 instead of for symbols n−n' . . . n−1 where t=n−n'−w, rather than: t=n−n'.

Figure 9:
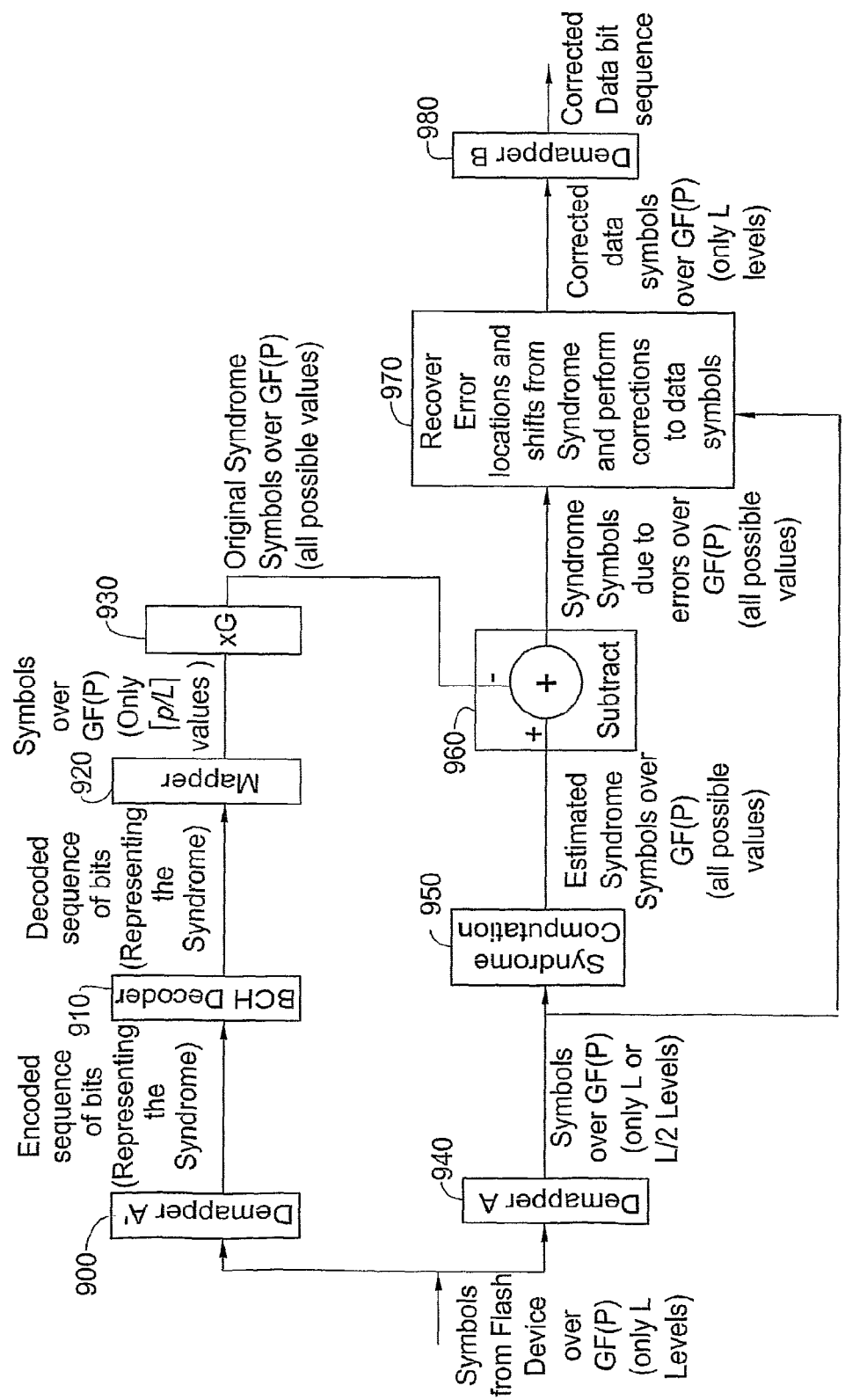
FIG. 9 is a simplified functional block diagram of a "syndrome separate & shortened, redundancy & data mixed" decoder constructed and operative in accordance with certain embodiments of the present invention.

FIG. 9 illustrates a "syndrome separate & shortened, redundancy & data mixed" decoder which is similar to the "syndrome separate, redundancy & data mixed" decoder of FIG. 5, however, in FIG. 9, a matrix multiplier unit xG (930) is provided which receives the output of w symbols of the Mapper unit (920) and multiplies it by the following matrix G:

$$G = \begin{pmatrix} \alpha^{(t+n')\cdot 0} & \alpha^{(t+n'+1)\cdot 0} & \alpha^{(t+n'+2)\cdot 0} & \cdots & \alpha^{(t+n'+w-1)\cdot 0} \\ \alpha^{(t+n')\cdot 1} & \alpha^{(t+n'+1)\cdot 1} & \alpha^{(t+n'+2)\cdot 1} & & \\ \alpha^{(t+n')\cdot 2} & \alpha^{(t+n'+1)\cdot 2} & \alpha^{(t+n'+2)\cdot 2} & & \\ \vdots & & & \ddots & \\ \alpha^{(t+n')\cdot (w-1)} & & & & \alpha^{(t+n'+w-1)\cdot (w-1)} \end{pmatrix}.$$

Demappers A' (900) and A (940) may be similar to Demappers A' (400) and A (430) in the "syndrome separate, redundancy & data mixed" decoder of FIG. 5, except that demixing is effected for symbols t . . . t+n'−1 instead of for symbols n−n' . . . n−1 where t=n−n'−w rather than t=n−n'. The Mapper unit (920) may be generally similar to the Mapper unit (420) in the "syndrome separate" decoder of FIG. 3 however during de-encapsulation, the parameter p is replaced with $\lceil p/L \rceil$ and the outputs are multiplied by L. In the "syndrome separate & shortened, redundancy & data mixed" decoder of FIG. 9, as opposed to its FIG. 5 counterpart for the "syndrome separate, redundancy & data mixed" code, the syndrome computation unit (950) operates over n=t+n'+w elements instead of t elements. The remaining units of FIG. 9 may be generally similar to their "syndrome separate, redundancy & data mixed" code counterparts in the embodiment of FIG. 5.

Parameter Determination in accordance with certain embodiments of the present invention is now described. A decoding error may occur if either one of the following events occurs:

1. An error occurs in the decoding of "accurate" Syndrome (910), e.g. there are more than $\lfloor (n'-k')/\lceil \log_2 n' \rceil \rfloor$ errors in the (n'=n−t−w) symbols allocated to store the redundancy. Now, the probability of bit error is given by $P_{cross}/(L/2)$.

2. An error occurs in the decoding of the data symbols using the Lee metric decoder (970), e.g. there were w or more errors in n symbols.

The probability of any of these events may be bounded from above by $$P_{err} \leq \sum_{i=\lfloor (n'-k')/\lceil \log_2 n' \rceil \rfloor + 1}^{n'} \frac{n'!}{i!(n'-i)!} \left(\frac{2}{L} P_{cross}\right)^i \left(1 - \frac{2}{L} P_{cross}\right)^{n'-i} + \sum_{i=w}^{n} \frac{n!}{i!(n-i)!} \left(\frac{2L-2}{L} P_{cross}\right)^i \left(1 - \frac{2L-2}{L} P_{cross}\right)^{n-i}$$

Thus, by enumerating over w, a value may be selected which reduces the above probability, e.g. to a minimum.

A numerical example for use of "syndrome separate & shortened, redundancy & data mixed" code is now described. In the following example, the number of levels is L=16, the code length is n=4352, the number of data bits to be encoded is k=16384, the number of symbols produced by Mapper A is t=5462, the prime number of the field is p=4357. the primitive element is α=2, the syndrome size is w=76, the number of bits encapsulated by mapper r is 122 (encapsulating 15 symbols with $\lceil p/L \rceil$ values each), the bit sequence to be encoded by the BCH is k'=619 bits long, the Bit sequence produced by the BCH is n'=719 bits long, the field over which the binary BCH was constructed is $GF(2^{10})$ and the prime polynomial constructing it is $X^{10}+X^3+1$. A code with the above parameters can handle $p_{cross}$=0.0036 and obtain a frame error rate of approximately 5e-13. The advantage of the above code, in comparison with other conventional coding schemes, is immediately apparent. The above cross over probability induces an un-coded bit error rate of 0.001688 if Gray coding is used; and it is appreciated that the code above did not actually require Gray coding. A frame error of 5E-13 would be obtained by an equivalent code which can correct up to 75 errors. However, using a conventional binary BCH code with the same number of spare cells (1024 bits) it is only possible to correct 68 errors.

Use of Lee distance based codes rather than Hamming distance based codes is a particular advantage in flash memory devices constructed and operative in accordance with certain embodiments of the present invention because if gray mapping is being used in a flash memory device, errors almost always involve a symbol being confounded with a neighboring symbol in the mapping scheme rather than with a distant symbol in the mapping scheme, such that use of Lee distance based code may give better error correction functionality per unit of redundancy or less redundancy for a given level of error correction functionality adequacy.

It is appreciated that software components of the present invention including programs and data may, if desired, be implemented in ROM (read only memory) form including CD-ROMs, EPROMs and EEPROMs, or may be stored in any other suitable computer-readable medium such as but not limited to disks of various kinds, cards of various kinds and RAMs. Components described herein as software may, alternatively, be implemented wholly or partly in hardware, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software.

Certain operations are described herein as occurring in the microcontroller internal to a flash memory device. Such description is intended to include operations which may be performed by hardware which may be associated with the microcontroller such as peripheral hardware on a chip on which the microcontroller may reside. It is also appreciated that some or all of these operations, in any embodiment, may alternatively be performed by the external, host-flash memory device interface controller including operations which may be performed by hardware which may be associated with the interface controller such as peripheral hardware on a chip on which the interface controller may reside. Finally it is appreciated that the internal and external controllers may each physically reside on a single hardware device, or alternatively on several operatively associated hardware devices.

Any data described as being stored at a specific location in memory may alternatively be stored elsewhere, in conjunction with an indication of the location in memory with which the data is associated. For example, instead of storing page- or erase-sector-specific information within a specific page or erase sector, the same may be stored within the flash memory device's internal microcontroller or within a microcontroller interfacing between the flash memory device and the host, and an indication may be stored of the specific page or erase sector associated with the cells.

It is appreciated that the teachings of the present invention can, for example, be implemented by suitably modifying, or interfacing externally with, flash controlling apparatus. The flash controlling apparatus controls a flash memory array and may comprise either a controller external to the flash array or a microcontroller on-board the flash array or otherwise incorporated therewithin. Examples of flash memory arrays include Samsung's K9XXG08UXM series, Hynix' HY27UK08BGFM Series, Micron's MT29F64G08TAAWP or other arrays such as but not limited to NOR or phase change memory. Examples of controllers which are external to the flash array they control include STMicroelectrocincs's ST7265x microcontroller family, STMicroelectrocincs's ST72681 microcontroller, and SMSC's USB97C242, Traspan Technologies' TS-4811, Chipsbank CBM2090/CBM1190. Example of commercial IP software for Flash file systems are: Denali's Spectra™ NAND Flash File System, Aarsan's NAND Flash Controller IP Core and Arasan's NAND Flash File System. It is appreciated that the flash controller apparatus need not be NAND-type and can alternatively, for example, be NOR-type or phase change memory-type.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Flash controlling apparatus, whether external or internal to the controlled flash array, typically includes the following components: a Memory Management/File system, a NAND interface (or other flash memory array interface), a Host Interface (USB, SD or other), error correction circuitry (ECC) typically comprising an Encoder and matching decoder, and a control system managing all of the above.

The present invention may for example interface with or modify, as per any of the embodiments described herein, one, some or all of the above components and particularly with the ECC component.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting.

We claim:

1. A method for operating a flash device, said method comprising:
reading, from flash memory cells the flash device, data symbols and redundancy symbols;
calculating syndrome symbols based on the redundancy symbols;
calculating estimated syndrome symbols based on at least the data symbols;
calculating differences between the syndrome symbols and corresponding estimated syndrome symbols to provide error syndromes; and calculating corrected data symbols in response to the data symbols, the error syndromes;
wherein the calculating of the corrected data symbols involves calculating Lee distances.

2. The method according to claim 1, wherein the calculating of the estimated syndrome symbols is based only on the data symbols.

3. The method according to claim 2, wherein the calculating of the syndrome symbols comprises applying a sequence of operations that comprise de-mapping, Bose Chaudhuri Hocquengham (BCH) decoding and mapping; and wherein the calculating of the estimated syndrome symbols comprises syndrome computation.

4. The method according to claim 3 wherein each flash memory cell of the flash memory cells stores up to L distinctive levels of charge; wherein if L differs from a power of two the de-mapping comprises de-encapsulating the redundancy symbols.

5. The method according to claim 1, wherein the calculating of the estimated syndrome symbols is based on the data symbols and on redundancy bits stripped from the redundancy symbols.

6. The method according to claim 5, wherein the calculating of the syndrome symbols comprises applying a sequence of operations that comprises de-mapping, Bose Chaudhuri Hocquengham (BCH) decoding and mapping; and
wherein the calculating of the estimated syndrome symbols comprises demapping and syndrome computation.

7. The method according to claim 1, wherein the calculating of the estimated syndrome symbols is based on the data symbols and on the redundancy symbols.

8. The method according to claim 7 wherein the calculating of the estimated syndrome symbols comprises syndrome computation; and
wherein the calculating of the syndrome symbols comprises applying a sequence of operations that comprises de-mapping, Bose Chaudhuri Hocquengham (BCH) decoding, mapping and multiplication by a Galois matrix;
wherein elements of the Galois matrix are powers of alpha, alpha being a non-zero primitive element of a Galois field in which the data symbols and the redundency symbols are elements.

9. The method according to claim 8 wherein r is a row index r, c is a column index, t being a number of data symbols, w being a number of redundancy syndromes, wherein r and c range between zero and (w−1), an element of the Galois matrix that belong to a r'th row and a c'th column of the Galois matrix equals alpha by a power of (t+c)*r.

10. The method according to claim 8 wherein r is a row index r, c is a column index, t being a number of data symbols, n' is a number of data bits that are represented by the data symbols, being a number of redundancy syndromes, wherein r and c range between zero and (w−1), an element of the Galois matrix that belong to a r'th row and a c'th column of the Galois matrix equals alpha by a power of (t+c+n')*r.

11. The method according to claim 7 wherein the calculating of the estimated syndrome symbols comprises demapping and syndrome computation; and
wherein the calculating of the syndrome symbols comprises applying a sequence of operations that comprises de-mapping, Bose Chaudhuri Hocquengham (BCH) decoding, mapping and multiplication by a Galois matrix;
wherein elements of the Galois matrix are powers of alpha, alpha being a non-zero primitive element of a Galois field in which the data symbols and the redundency symbols are elements.

12. A program storage device readable by machine, tangibly embodying a program of instructions executable by the machine to perform method steps of:

reading, from flash memory cells the flash device, data symbols and redundancy symbols;
calculating syndrome symbols based on the redundancy symbols;
calculating estimated syndrome symbols based on at least the data symbols;
calculating differences between the syndrome symbols and corresponding estimated syndrome symbols provide error syndromes; and calculating corrected data symbols in response to the data symbols, the error syndromes;
wherein the calculating of the corrected data symbols involves calculating Lee distances.

13. A decoder comprising:
a first circuit for calculating syndrome symbols based on redundancy symbols read from a flash memory array;
a second circuit for calculating estimated syndrome symbols based on at least data symbols read from the flash memory array;
a subtraction unit arranged to calculate differences between the syndrome symbols and corresponding estimated syndrome symbols to provide error syndromes; and
a recovery block that is arranged to calculate corrected data symbols in response to the data symbols, the error syndromes by calculating Lee distances.

14. The decoder according to claim 13, wherein the calculating of the estimated syndrome symbols is based only on the data symbols.

15. The decoder according to claim 13, wherein the first circuit comprises a de-mapper, a Bose Chaudhuri Hocquengham (BCH) decoder and a mapper; and wherein the second circuit comprises a syndrome computation unit.

16. The decoder according to claim 15 wherein each flash memory cell of the flash memory cells stores up to L distinctive levels of charge; wherein if L differs from a power of two then de-mapper is arranged to de-encapsulate the redundancy symbols.

17. The decoder according to claim 13, wherein the calculating of the estimated syndrome symbols is based on the data symbols and on redundancy bits stripped from the redundancy symbols.

18. The decoder according to claim 17, wherein the first circuit comprises a de-mapper, a Bose Chaudhuri Hocquengham (BCH) decoder and a mapper; and wherein the second circuit comprises another de-mapper and a syndrome computation unit.

19. The decoder according to claim 13, wherein the calculating of the estimated syndrome symbols is based on the data symbols and on the redundancy symbols.

20. The decoder according to claim 19 wherein the second circuit comprises a syndrome computation unit; and
wherein the first circuit comprises a de-mapper, a Bose Chaudhuri Hocquengham (BCH) decoder, a mapper and a matrix multiplier;
wherein the matrix multiplier is arranged to receive symbols from the mapper and to multiply the symbols by a Galois matrix;
wherein elements of the Galois matrix are powers of alpha, alpha being a non-zero primitive element of a Galois field in which the data symbols and the redundency symbols are elements.

21. The decoder according to claim 20 wherein r is a row index r, c is a column index, t being a number of data symbols, w being a number of redundancy syndromes, wherein r and c range between zero and (w−1), an element of the Galois matrix that belong to a r'th row and a c'th column of the Galois matrix equals alpha by a power of (t+c)*r.

22. The decoder according to claim 19 wherein the first circuit comprises a de-mapper, a Bose Chaudhuri Hocquengham (BCH) decoder, a mapper and a matrix multiplier;
- wherein the second circuit comprises another de-mapper and a syndrome computation unit;
- wherein the matrix multiplier is arranged to receive symbols from the mapper and to multiply the symbols by a Galois matrix;
- wherein elements of the Galois matrix are powers of alpha, alpha being a non-zero primitive element of a Galois field in which the data symbols and the redundancy symbols are elements.

23. The decoder according to claim 22 wherein r is a row index r, c is a column index, t being a number of data symbols, n' is a number of data bits that are represented by the data symbols, being a number of redundancy syndromes, wherein r and c range between zero and (w−1), and an element of the Galois matrix that belong to a r'th row and a c'th column of the Galois matrix equals alpha by a power of (t+c+n')*r.

* * * * *